United States Patent
Phillips

(10) Patent No.: US 11,751,860 B2
(45) Date of Patent: *Sep. 12, 2023

(54) METHODS AND SYSTEMS FOR SEALING A PUNCTURE OF A VESSEL

(71) Applicant: Phillips Medical, LLC, Jefferson City, MO (US)

(72) Inventor: Victor Matthew Phillips, Jefferson City, MO (US)

(73) Assignee: Phillips Medical, LLC, Jefferson City, MO (US)

(*) Notice: Subject to any disclaimer, the term of this patent is extended or adjusted under 35 U.S.C. 154(b) by 73 days.

This patent is subject to a terminal disclaimer.

(21) Appl. No.: 17/509,319

(22) Filed: Oct. 25, 2021

(65) Prior Publication Data

US 2022/0039782 A1 Feb. 10, 2022

Related U.S. Application Data

(60) Continuation of application No. 16/563,295, filed on Sep. 6, 2019, now Pat. No. 11,185,318, which is a (Continued)

(51) Int. Cl.
*A61B 17/00* (2006.01)

(52) U.S. Cl.
CPC .... *A61B 17/0057* (2013.01); *A61B 17/00234* (2013.01); *A61B 2017/0038* (2013.01); (Continued)

(58) Field of Classification Search
CPC .......... A61B 17/00234; A61B 17/0057; A61B 2017/0038; A61B 2017/00592; (Continued)

(56) References Cited

U.S. PATENT DOCUMENTS 5,342,393 A 8/1994 Stack
6,136,010 A 10/2000 Modesitt et al.
(Continued)

FOREIGN PATENT DOCUMENTS

EP 138761 A2 4/1985
EP 2166953 A2 3/2010
(Continued)

OTHER PUBLICATIONS

Extended European Search Report, dated Dec. 10, 2020, for EP patent application No. EP 18798242.6 (10 pgs ).

*Primary Examiner* — Majid Jamialahmadi
(74) *Attorney, Agent, or Firm* — Armstrong Teasdale LLP

(57) ABSTRACT

A system to facilitate sealing a puncture of a vessel includes an implant having first and second expandable sections, and a delivery device that includes an inner tube and a circumscribing outer tube. The outer tube defines a first lumen configured to retain the implant, and a second lumen configured to channel fluid from the vessel through a distal opening proximal to the implant. A pusher circumscribed at least partially by the outer tube is configured to compress the implant to selectively expand the first and second expandable sections. The outer tube is selectively retractable relative to the inner tube such that the first expandable section remains substantially within the first lumen and the second expandable section is positioned outside of the first lumen. The outer tube is further selectively retractable relative to the inner tube such that the first expandable section is positioned outside of the first lumen.

14 Claims, 20 Drawing Sheets

Related U.S. Application Data division of application No. 15/183,954, filed on Jun. 16, 2016, now Pat. No. 10,448,938.

(52) U.S. Cl.
CPC .............. *A61B 2017/00592* (2013.01); *A61B 2017/00606* (2013.01); *A61B 2017/00619* (2013.01); *A61B 2017/00623* (2013.01); *A61B 2017/00778* (2013.01)

(58) Field of Classification Search
CPC ........... A61B 2017/00606; A61B 2017/00619; A61B 2017/00623; A61B 2017/00646; A61B 2017/00575; A61B 2017/00637
See application file for complete search history.

(56) References Cited

U.S. PATENT DOCUMENTS

| | | |
|---|---|---|
| 6,183,496 B1 | 2/2001 | Urbanski |
| 6,333,787 B1 | 12/2001 | Konno |
| 6,366,742 B1 | 4/2002 | Heiner et al. |
| 6,461,366 B1 | 10/2002 | Seguin |
| 6,529,598 B1 | 3/2003 | Sacca et al. |
| 6,556,954 B1 | 4/2003 | Denk et al. |
| 6,582,452 B2 | 6/2003 | Coleman et al. |
| 6,616,686 B2 | 9/2003 | Coleman et al. |
| 6,669,714 B2 | 12/2003 | Coleman et al. |
| 6,770,083 B2 | 8/2004 | Seguin |
| 6,926,731 B2 | 8/2005 | Coleman et al. |
| 7,001,400 B1 | 2/2006 | Modesitt et al. |
| 7,008,435 B2 | 3/2006 | Cummins |
| 7,048,754 B2 | 5/2006 | Martin et al. |
| 7,111,768 B2 | 9/2006 | Cummins et al. |
| 7,163,551 B2 | 1/2007 | Anthony et al. |
| 7,288,097 B2 | 10/2007 | Seguin |
| 7,682,369 B2 | 3/2010 | Seguin |
| 7,753,935 B2 | 7/2010 | Brett et al. |
| 7,837,696 B2 | 11/2010 | Modesitt et al. |
| 7,850,701 B2 | 12/2010 | Modesitt et al. |
| 7,850,709 B2 | 12/2010 | Cummins et al. |
| 7,981,139 B2 | 7/2011 | Martin et al. |
| 8,048,108 B2 | 11/2011 | Sibbitt, Jr. et al. |
| 8,057,491 B2 | 11/2011 | Modesitt et al. |
| 8,192,459 B2 | 6/2012 | Cummins et al. |
| 8,323,298 B2 | 12/2012 | Modesitt et al. |
| 8,333,787 B2 | 12/2012 | Pipenhagen et al. |
| 8,366,742 B2 | 2/2013 | Coleman et al. |
| 8,398,676 B2 | 3/2013 | Roorda et al. |
| 8,469,995 B2 | 6/2013 | Cummins et al. |
| 8,529,598 B2 | 9/2013 | Jenson et al. |
| 8,556,954 B2 | 10/2013 | Ben Muvhar et al. |
| 8,590,760 B2 | 11/2013 | Cummins et al. |
| 8,657,852 B2 | 2/2014 | Roorda et al. |
| 8,758,397 B2 | 6/2014 | Sibbitt, Jr. et al. |
| 8,784,447 B2 | 7/2014 | Coleman et al. |
| 8,845,682 B2 | 9/2014 | Penner et al. |
| 8,906,050 B2 | 12/2014 | Brett et al. |
| 8,920,442 B2 | 12/2014 | Sibbitt, Jr. et al. |
| 8,932,324 B2 | 1/2015 | Sibbitt, Jr. et al. |
| 9,060,751 B2 | 6/2015 | Martin et al. |
| 9,060,769 B2 | 6/2015 | Coleman et al. |
| 9,089,311 B2 | 7/2015 | Fortson et al. |
| 9,131,932 B2 | 9/2015 | Fegels |
| 9,173,644 B2 | 11/2015 | Voss |
| 9,192,352 B2 | 11/2015 | Yao et al. |
| 9,192,362 B2 | 11/2015 | Paul, Jr. et al. |
| 9,241,696 B2 | 1/2016 | Mehl |
| 9,295,469 B2 | 3/2016 | Cummins et al. |
| 9,314,230 B2 | 4/2016 | Roorda et al. |
| 9,402,625 B2 | 8/2016 | Coleman et al. |
| 9,414,820 B2 | 8/2016 | Voss et al. |
| 9,414,824 B2 | 8/2016 | Fortson et al. |
| 9,456,811 B2 | 10/2016 | Sibbitt, Jr. et al. |
| 9,486,191 B2 | 11/2016 | Gianotti et al. |
| 9,572,558 B2 | 2/2017 | Grant et al. |
| 9,610,070 B2 | 4/2017 | Martin et al. |
| 9,662,099 B2 | 5/2017 | Grant et al. |
| 9,675,336 B2 | 6/2017 | Weisel et al. |
| 9,737,286 B2 | 8/2017 | Grant et al. |
| 2002/0002373 A1 | 1/2002 | Boehlke et al. |
| 2002/0026215 A1 | 2/2002 | Redmond et al. |
| 2005/0273135 A1 | 12/2005 | Chanduszko et al. |
| 2006/0142784 A1 | 6/2006 | Kontos |
| 2006/0190036 A1 | 8/2006 | Wendel et al. |
| 2006/0287673 A1 | 12/2006 | Brett et al. |
| 2007/0021778 A1 | 1/2007 | Carly |
| 2007/0060895 A1 | 3/2007 | Sibbitt, Jr. et al. |
| 2008/0091264 A1 | 4/2008 | Machold et al. |
| 2008/0269801 A1 | 10/2008 | Coleman et al. |
| 2009/0171446 A1 | 7/2009 | Ainsworth et al. |
| 2009/0230168 A1 | 9/2009 | Coleman et al. |
| 2009/0248064 A1* | 10/2009 | Preinitz ............. A61B 17/0057 606/213 |
| 2010/0152748 A1 | 6/2010 | Penner et al. |
| 2010/0152772 A1 | 6/2010 | Brett et al. |
| 2010/0168767 A1 | 7/2010 | Yassinzadeh et al. |
| 2010/0179567 A1 | 7/2010 | Voss et al. |
| 2010/0179589 A1 | 7/2010 | Roorda et al. |
| 2010/0185234 A1 | 7/2010 | Fortson et al. |
| 2010/0228239 A1 | 9/2010 | Freed |
| 2011/0137338 A1 | 6/2011 | Phillips |
| 2011/0213410 A1 | 9/2011 | Ginn et al. |
| 2011/0218568 A1 | 9/2011 | Voss |
| 2011/0224713 A1 | 9/2011 | Fortson |
| 2011/0224728 A1 | 9/2011 | Martin et al. |
| 2012/0165854 A1 | 6/2012 | Pipenhagen et al. |
| 2012/0245597 A1 | 9/2012 | Tegels |
| 2012/0253387 A1 | 10/2012 | Teichman et al. |
| 2012/0296275 A1 | 11/2012 | Martin et al. |
| 2014/0046428 A1 | 2/2014 | Cragg et al. |
| 2014/0094929 A1 | 4/2014 | Shin et al. |
| 2014/0345109 A1 | 11/2014 | Grant et al. |
| 2015/0066055 A1 | 3/2015 | Sibbitt, Jr. et al. |
| 2015/0088240 A1 | 3/2015 | Lam et al. |
| 2015/0094759 A1 | 4/2015 | Wolinsky et al. |
| 2015/0119928 A1 | 4/2015 | Penner et al. |
| 2015/0119929 A1 | 4/2015 | Penner et al. |
| 2015/0265261 A1 | 9/2015 | Alokaili |
| 2015/0282791 A1 | 10/2015 | Phillips et al. |
| 2016/0000417 A1 | 1/2016 | Voss |
| 2016/0051239 A1 | 2/2016 | Martin et al. |
| 2016/0051258 A1 | 2/2016 | Cummins et al. |
| 2016/0120415 A1 | 5/2016 | Webler et al. |
| 2016/0151057 A1 | 6/2016 | Voss |
| 2016/0151613 A1 | 6/2016 | Penner et al. |
| 2016/0166241 A1 | 6/2016 | Mcgoldrick et al. |
| 2016/0174953 A1 | 6/2016 | Grant et al. |
| 2016/0213357 A1 | 7/2016 | Mehl |
| 2017/0020517 A1 | 1/2017 | Coleman et al. |
| 2017/0049426 A1 | 2/2017 | Gianotti et al. |
| 2017/0086806 A1 | 3/2017 | Sibbitt, Jr. et al. |
| 2017/0181736 A1 | 6/2017 | McGoldrick et al. |
| 2017/0209131 A1 | 7/2017 | Penner et al. |
| 2017/0281142 A1 | 10/2017 | Martin et al. |

FOREIGN PATENT DOCUMENTS

| | | |
|---|---|---|
| EP | 1879505 B1 | 10/2012 |
| EP | 2519161 A2 | 11/2012 |
| EP | 2658453 A2 | 11/2013 |
| EP | 2709712 A2 | 3/2014 |
| EP | 2260770 B1 | 7/2014 |
| EP | 2819586 A2 | 1/2015 |
| EP | 2996573 A1 | 3/2016 |
| EP | 3232938 A1 | 10/2017 |
| EP | 3232939 A1 | 10/2017 |
| WO | 2000033744 A1 | 6/2000 |
| WO | 2006117766 A2 | 11/2006 |
| WO | 2008152617 A2 | 12/2008 |
| WO | 2011080588 A2 | 7/2011 |
| WO | 2012090069 A2 | 7/2012 |
| WO | 2012156819 A2 | 11/2012 |
| WO | 2013128292 A2 | 9/2013 |

(56) References Cited

FOREIGN PATENT DOCUMENTS

| WO | 2014141209 A1 | 9/2014 |
| WO | 2016096930 A1 | 6/2016 |
| WO | 2016096932 A1 | 6/2016 |
| WO | 2017102941 A1 | 6/2017 |

* cited by examiner

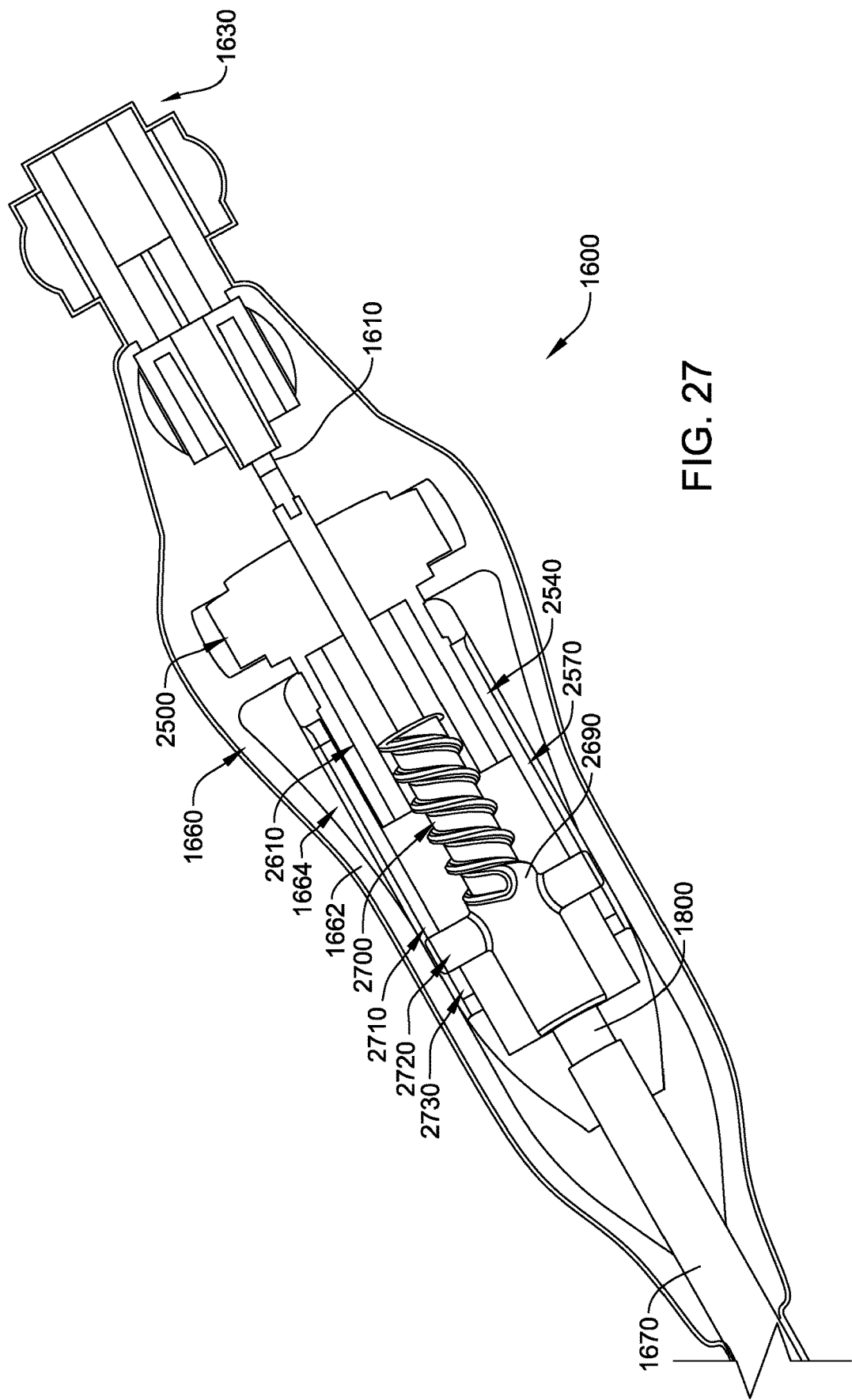

METHODS AND SYSTEMS FOR SEALING A PUNCTURE OF A VESSEL

CROSS REFERENCE TO RELATED APPLICATIONS

This application is a continuation of and claims priority to U.S. application Ser. No. 16/563,295, filed Sep. 6, 2019, entitled "METHODS AND SYSTEMS FOR SEALING A PUNCTURE OF A VESSEL," which is a divisional of and claims priority to U.S. application Ser. No. 15/183,954, filed Jun. 16, 2016, entitled "METHODS AND SYSTEMS FOR SEALING A PUNCTURE OF A VESSEL," the contents of each of which are hereby incorporated by reference in their entirety.

BACKGROUND

The subject matter described herein relates generally to medical devices and, more particularly, to methods and systems for sealing a puncture of a vessel.

Catheter introducers are known to provide access to an artery for at least some medical procedures including, without limitation, cardiac catheterizations and peripheral endovascular procedures. After conducting such medical procedures, the catheter introducer is removed from the access site, leaving an arterial opening. At least some body fluids including, without limitation, blood are discharged from the arterial opening. Excess blood loss may endanger and/or traumatize the patient. One known method of controlling blood loss is through direct manual pressure over the arterial opening. However, in at least some cases, such as but not limited to medical procedures that require large-bore access through the artery wall, manual pressure alone is not sufficient to achieve hemostasis. For example, at least some such procedures are performed using catheter introducers of 9 Fr to 24 Fr diameter.

Another known method of controlling blood loss at a puncture site is the insertion of an implant, such as an anchor, balloon, disk, or the like, inside the lumen of the artery. The implant is then pulled back within the lumen and against the inner wall of the artery at the puncture site. The implant has a diameter at least slightly greater than the puncture opening, enabling the implant to be positioned to block blood loss through the puncture. However, in at least some cases, such as but not limited to medical procedures that require large-bore access through the artery wall, the required diameter of the implant approaches a diameter of the artery itself, increasing a risk that the implant may encounter an obstacle inside the artery that inhibits proper positioning, such as plaque, a smaller side branch of the artery, or the walls of the artery itself. For example, at least some such procedures result in puncture openings up to 8 millimeters in diameter, and the common femoral artery has an average diameter of 7 to 8 millimeters. Moreover, in at least some cases, such as but not limited to medical procedures that require large-bore access through the artery wall, the insertion of the catheter introducer creates an inferior flap in the artery wall, and if the inferior flap is not elevated during the deployment of the implant, there is a risk that the inferior flap will prevent a sufficient seal of the puncture site or obstruct the femoral artery.

BRIEF SUMMARY

In one aspect, a method for sealing a puncture of a vessel using an implant deployed by a delivery device is provided. The delivery device includes an inner tube and an outer tube circumscribing at least a portion of the inner tube. The implant is retained in a delivery configuration within a first lumen of the outer tube. The method includes advancing a distal end of the delivery device into the vessel until a fluid is channeled through a distal opening of the outer tube into a second lumen of the outer tube. The distal opening is longitudinally located one of (i) adjacent to the implant and (ii) proximal to the implant. The method also includes retracting the outer tube relative to the inner tube, such that a first expandable section of the implant remains substantially within the first lumen and a second expandable section of the implant is positioned outside of the first lumen. The method further includes compressing the implant such that the second expandable section is expanded, and the first expandable section remains in the delivery configuration. Additionally, the method includes withdrawing the delivery device until the expanded second expandable section abuts an interior surface of a wall of the vessel, and retracting the outer tube relative to the inner tube, such that the first expandable section of the implant is positioned outside of the first lumen. The method also includes further compressing the implant such that the first expandable section is expanded.

In another aspect, a system to facilitate sealing a puncture of a vessel is provided. The system includes an implant that includes a first expandable section and a second expandable section. The system also includes a delivery device that includes an inner tube and an outer tube circumscribing at least a portion of the inner tube. The outer tube defines a first lumen configured to retain the implant in a delivery configuration, and a second lumen configured to channel a fluid from the vessel through a distal opening of the second lumen. The distal opening is longitudinally located one of (i) adjacent to the implant and (ii) proximal to the implant. The delivery device further includes a pusher circumscribed at least partially by the outer tube and configured to compress the implant to selectively expand each of the second expandable section and the first expandable section. The outer tube is selectively retractable relative to the inner tube such that the first expandable section remains substantially within the first lumen and the second expandable section is positioned outside of the first lumen. The outer tube is further selectively retractable relative to the inner tube such that the first expandable section is positioned outside of the first lumen.

The features, functions, and advantages described herein may be achieved independently in various embodiments of the present disclosure or may be combined in yet other embodiments, further details of which may be seen with reference to the following description and drawings.

BRIEF DESCRIPTION OF THE DRAWINGS

FIG. 27 is a third cut-away view of the delivery device of FIG. 25;

DETAILED DESCRIPTION

The methods and apparatus described herein relate to medical devices and, more particularly, to a system and method for use in sealing a puncture of a vessel. The system includes an implant deployed by a delivery device. More specifically, in at least one embodiment, the system includes an implant with two separately expandable sections. The delivery device delivers the implant to the puncture site and into the vessel in a collapsed, or delivery, configuration within a lumen of an outer tube. The outer tube is selectively retractable, such that the first expandable section remains substantially within the lumen while the second expandable section is exposed outside the lumen. Without the constraint of the outer tube surrounding the second expandable section, a compressive force on the implant exerted by the delivery device expands the second expandable section. The delivery device is withdrawn until the expanded second section abuts the interior of the vessel wall, positioning the first expandable section outside the vessel wall. The outer tube is further selectively retractable, such that the first expandable section is also exposed outside the lumen. Without the constraint of the outer tube surrounding the first expandable section, a compressive force on the implant exerted by the delivery device expands the first expandable section, such that the first and second expanded sections are disposed on opposing sides of the vessel wall to occlude the puncture site.

In some embodiments, a flexible skirt adjacent the second section further facilitates occluding the puncture site. In certain embodiments, the implant includes a locking mechanism configured to lock the sections in the expanded configuration at the puncture site after the delivery device is withdrawn. In some embodiments, the outer tube includes a second lumen configured to channel fluid from the vessel through a distal opening longitudinally located one of (i) adjacent to the implant and (ii) proximal to the implant, to provide a visual indication that the delivery device is properly positioned for expansion of the implant.

As used herein, an element or step recited in the singular and preceded with the word "a" or "an" should be understood as not excluding plural said elements or steps, unless such exclusion is explicitly stated. Further, references to an "embodiment" or an "implementation" are not intended to be interpreted as excluding the existence of additional embodiments or implementations that also incorporate the recited features. Moreover, unless explicitly stated to the contrary, embodiments or implementations "comprising," "including," or "having" an element or a plurality of elements having a particular property may include additional such elements not having that property.

Figure 1:
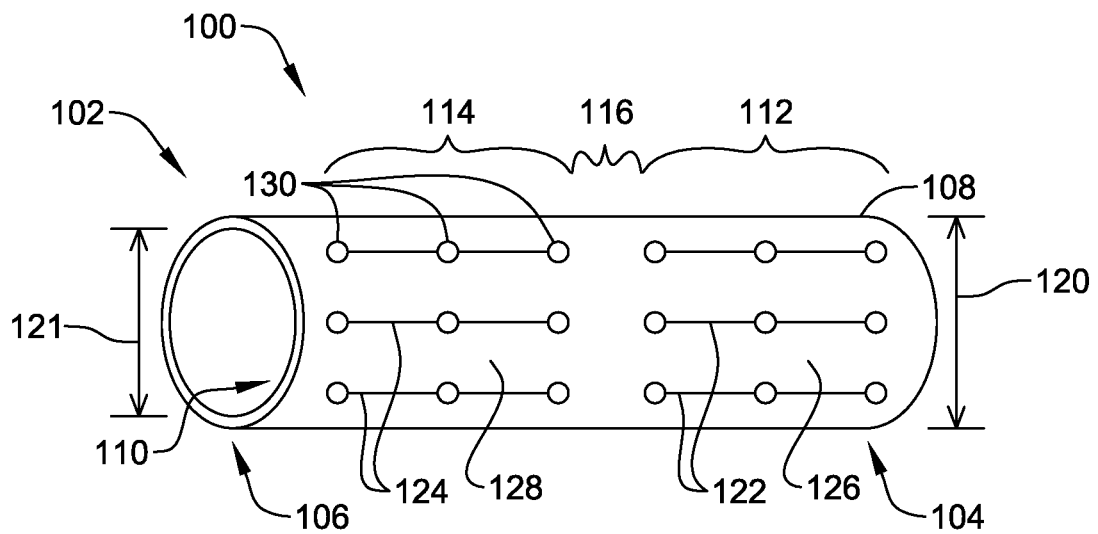
FIG. 1 is a perspective view of a first exemplary embodiment of an implant for facilitating hemostasis at a puncture site of an artery wall, showing the implant in a delivery configuration.

FIG. 1 is a perspective view of a first exemplary embodiment of an implant 100 for facilitating hemostasis at a puncture site of an artery wall, showing implant 100 in a delivery configuration. More specifically, implant 100 is illustrated in FIG. 1 in a delivery configuration 102. In the exemplary embodiment, implant 100 includes a generally tube-shaped body 108 that extends from a proximal end 104 to a distal end 106. Body 108 defines an interior lumen 110 extending therethrough from proximal end 104 to distal end 106. In certain embodiments, implant lumen 110 is sized to allow passage of a suitable portion of a delivery device, such as but not limited to an inner tube 1610 and a hypo tube 1700 (shown in FIG. 16), therethrough.

In the exemplary embodiment, implant 100 is formed from a bioabsorbable polymer. For example, but not by way of limitation, implant 100 is formed from at least one of a polylactic acid (PLA) and a polyglycolic acid (PGA), such that implant 100 is completely absorbable by a subject's body over a suitable period of time. In alternative embodiments, implant 100 is formed from any suitable material that enables implant 100 to function as described herein.

Figure 29:
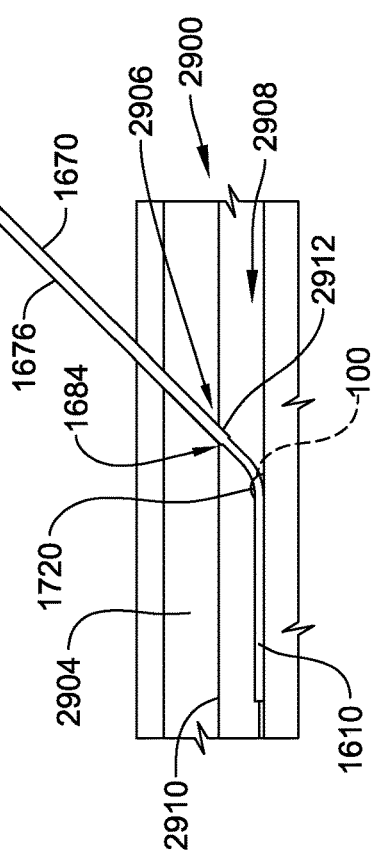
FIG. 29 illustrates a first stage of the method of FIGS. 28A and 28B.

Implant 100 in delivery configuration 102 is sized for insertion through a puncture site in an artery into a lumen of the artery (shown in FIG. 29). For example, in certain embodiments, implant 100 is sized for use at a puncture site associated with a sheath having a diameter in a range of about 9 Fr to about 24 Fr. In alternative embodiments, implant 100 is sized for use at a puncture site associated with a sheath having any suitable diameter. Implant 100 has a delivery diameter 120 suitable for insertion through the puncture site, and has an inner diameter 121 that is slightly less than delivery diameter 120.

Figure 4:
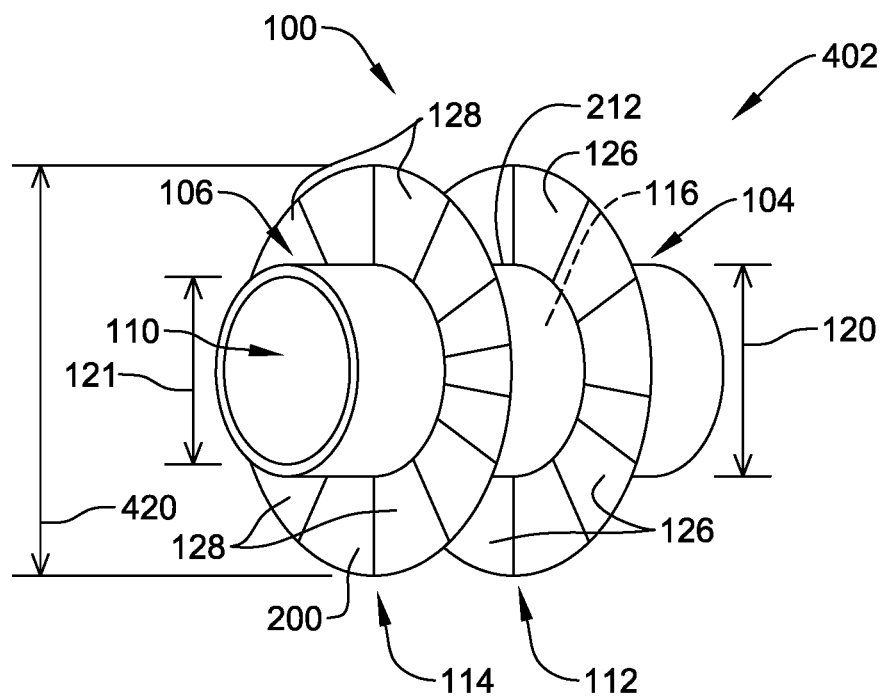
FIG. 4 is a perspective view of the implant of FIG. 1 in an expanded configuration.

FIG. 4 is a perspective view of implant 100 in an expanded configuration 402. With reference to FIGS. 1 and 4, implant 100 includes a first expandable section 112 adjacent proximal end 104, and a second expandable section 114 adjacent distal end 106. Each of first expandable section 112 and second expandable section 114 is selectively expandable radially outward from equal to, or less than, delivery diameter 120 to an expanded outer diameter 420. Expanded diameter 420 is sized to be greater than the diameter of the opening in the wall of the artery at the puncture site, such that after implant 100 in delivery configuration 102 is deployed longitudinally into the puncture opening, first expandable section 112 and second expandable section 114 are selectively expandable on opposing sides of the artery wall to facilitate sealing the puncture opening, and/or to restrict further longitudinal movement of implant 100 and thereby facilitate retaining implant 100 within the puncture opening, as will be described herein. In the exemplary embodiment, inner diameter 121 of implant 100 in expanded configuration 402 is approximately equal to inner diameter 121 of implant 100 in delivery configuration 102. In alternative embodiments, inner diameter 121 of implant 100 in expanded configuration 402 differs from inner diameter 121 of implant 100 in delivery configuration 102 in any suitable fashion that enables implant 100 to function as described herein.

In the exemplary embodiment, first expandable section 112 is defined by a first plurality of longitudinally extending cuts 122 defined in body 108. More specifically, longitudinal cuts 122 are spaced circumferentially about body 108, and each cut 122 extends radially therethrough body 108. Second expandable section 114 is similarly defined by a second plurality of longitudinally extending cuts 124 spaced circumferentially about body 108, such that each cut 124 extends radially therethrough body 108. Each pair of circumferentially adjacent longitudinal cuts 122 cooperates to define a respective one of a first plurality of expandable struts 126 therebetween, and each pair of circumferentially adjacent longitudinal cuts 124 cooperates to define a respective one of a second plurality of expandable struts 128 therebetween. Expandable struts 126 and 128 are configured to bulge radially outward in response to a compressive force applied longitudinally to implant 100, thereby expanding sections 112 and 114 to expanded diameter 420. In alternative embodiments, each of first expandable section 112 and second expandable section 114 is configured to selectively expand radially outward in any suitable fashion that enables implant 100 to function as described herein.

In the exemplary embodiment, stress relief regions 130 are defined in body 108 at each opposing end of each longitudinal cut 122 and 124, and at approximately the middle of each longitudinal cut 122 and 124. Stress relief regions 130 facilitate articulation of expandable struts 126 and 128 by creating weak regions in body 108 proximate the ends and middle of each strut 126 and 128, facilitating bending of struts 126 and 128 at the ends and middle in response to a compressive force. In the exemplary embodiment, stress relief regions 130 are formed from generally circular cutouts extending radially therethrough body 108. In alternative embodiments, stress relief regions 130 are formed in any suitable fashion. In other alternative embodiments, implant 100 does not include stress relief regions 130.

In the exemplary embodiment, body 108 includes a middle section 116 positioned longitudinally between first expandable section 112 and second expandable section 114. A diameter of middle section 116 remains less than or equal to delivery diameter 120 after expandable sections 112 and 114 are selectively expanded to expanded diameter 420. In alternative embodiments, body 108 does not include middle section 116.

Figure 2:
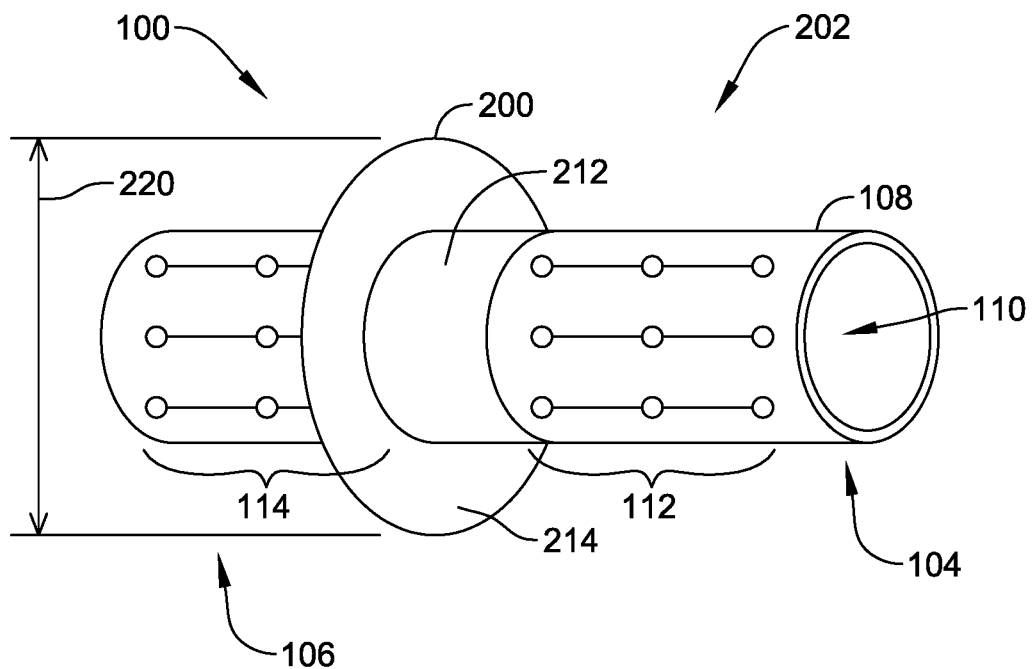
FIG. 2 is a perspective view of an exemplary skirt coupled to the implant of FIG. 1, showing the skirt in an expanded configuration.
Figure 3:
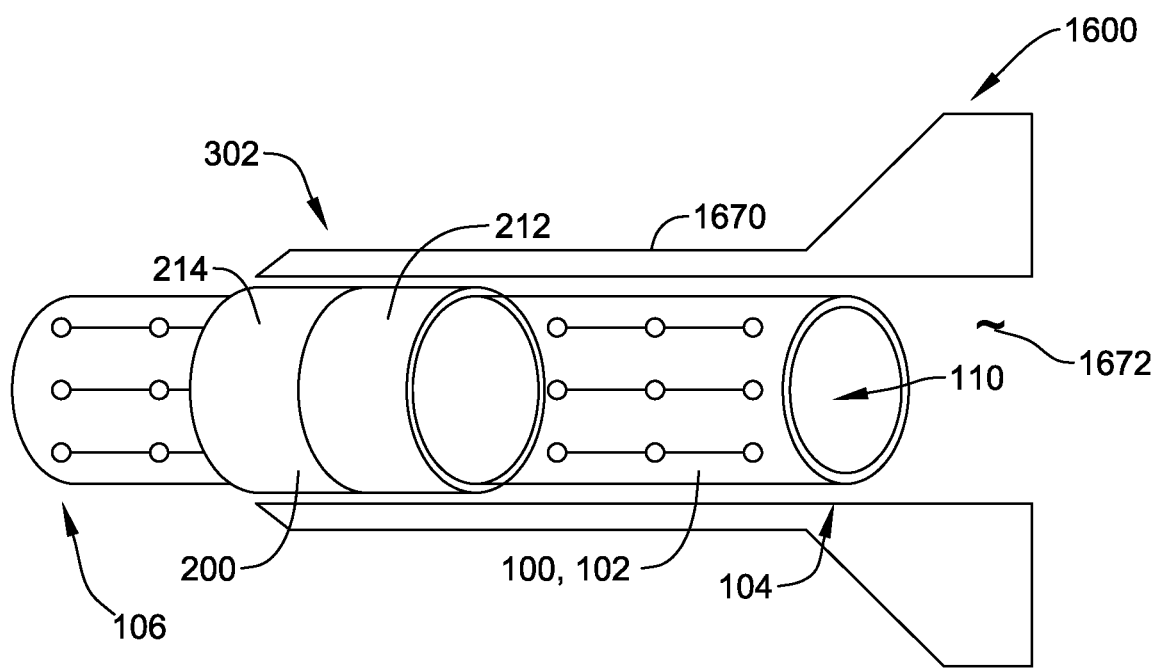
FIG. 3 is a perspective view of the implant of FIG. 1 including the skirt of FIG. 2 in a delivery configuration.

FIG. 2 is a perspective view of an exemplary skirt 200 coupled to implant 100. More specifically, skirt 200 is illustrated in an expanded configuration 202 in FIG. 2. FIG. 3 is a perspective view of implant 100 including skirt 200 in a delivery configuration 302. With reference to FIGS. 1-4, skirt 200 in delivery configuration 302 has a generally tubular shape with pleats, and is coupled concentrically adjacent an outer surface of body 108. In the exemplary embodiment, skirt 200 is formed from a bioabsorbable material as discussed above.

In the exemplary embodiment, skirt 200 includes a first portion 212 coupled to middle section 116 of body 108, and a second portion 214 coupled to, and distal from, first portion 212. In expanded configuration 202, second portion 214 is flared radially outward from body 108, generally into a disk shape normal to the longitudinal direction of implant 100 and having a diameter 220. As best seen in FIG. 4, diameter 220 is approximately equal to diameter 420 of second expandable section 114, and second portion 214 in expanded configuration 202 is configured for positioning adjacent second expandable section 114 in expanded configuration 402, such that second portion 214 facilitates occluding blood flow from the lumen of the artery through the puncture site, such as through gaps between struts 128 in expanded configuration 402, when implant 100 is positioned within the puncture opening. For example, but not by way of limitation, skirt 200 is formed from a flexible membrane that enables second portion 214 to transition from delivery configuration 302 to expanded configuration 202. In alternative embodiments, skirt 200 has any suitable structure that enables skirt 200 to function as described herein. Additionally or alternatively, implant 100 includes a similar skirt (not shown) configured for positioning adjacent first expandable section 112 to further facilitate occluding blood flow from the lumen of the artery through the puncture site.

In certain embodiments, implant 100 is configured for deployment by a delivery device 1600, portions of which are illustrated schematically in cutaway view in FIG. 3. Implant 100 is initially stowed in a first lumen 1672 of an outer tube 1670 of delivery device 1600, and outer tube 1670 retains second portion 214 in delivery configuration 302. When implant 100 is positioned within the lumen of the artery and outer tube 1670 is retracted relative to inner tube 1610, as will be described herein, second portion 214 is free to expand into expanded configuration 202. In some such embodiments, second portion 214 is urged into expanded configuration 202 through contact with second expandable section 114 as second expandable section 114 is transitioned to expanded configuration 402. Additionally or alternatively, second portion 214 is coupled to struts 128 of second expandable section 114 to facilitate the transition of second portion 214 into expanded configuration 202. In alternative embodiments, second portion 214 is transitioned into expanded configuration 202 in any suitable fashion that enables skirt 200 to function as described herein.

In alternative embodiments, implant 100 does not include skirt 200.

Figure 5:
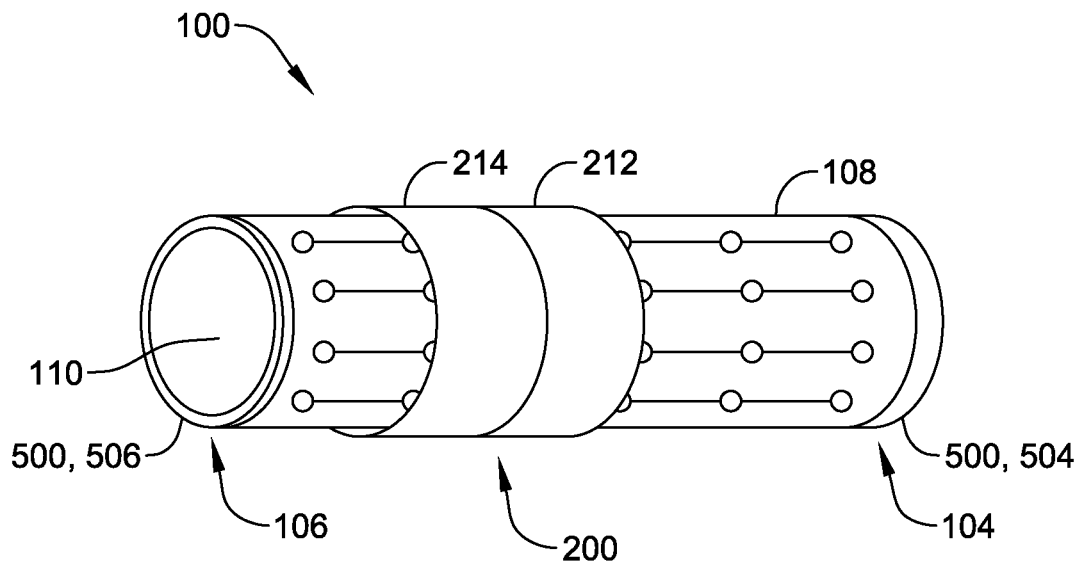
FIG. 5 is a perspective view of the implant of FIG. 1 coupled to opposing end caps that cooperate to form a first exemplary embodiment of an implant locking mechanism.
Figure 6:
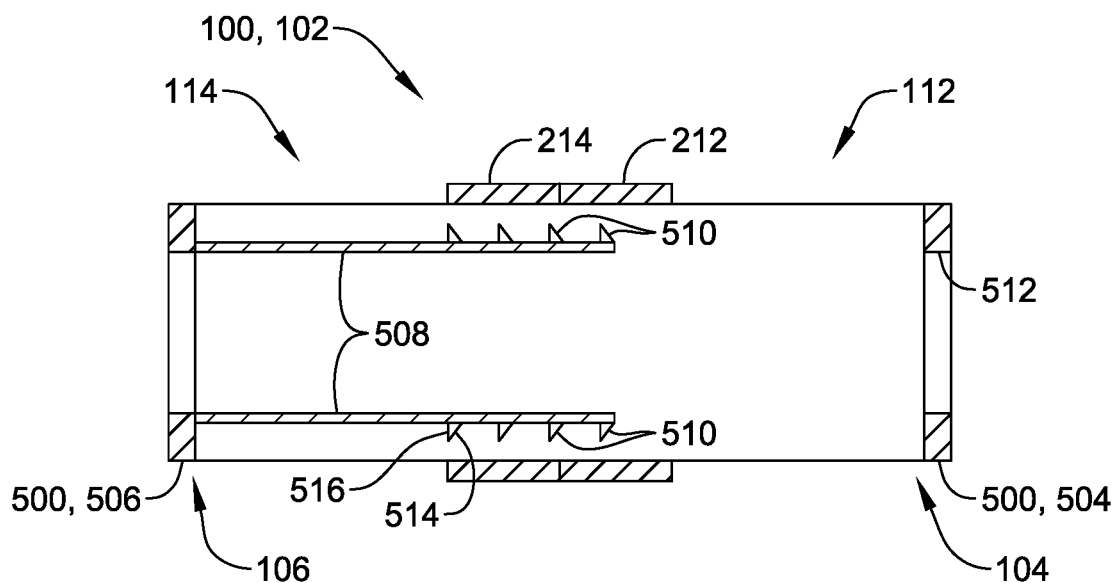
FIG. 6 is a sectional view of the implant and locking mechanism of FIG. 5, showing the implant in the delivery configuration of FIG. 1.
Figure 7:
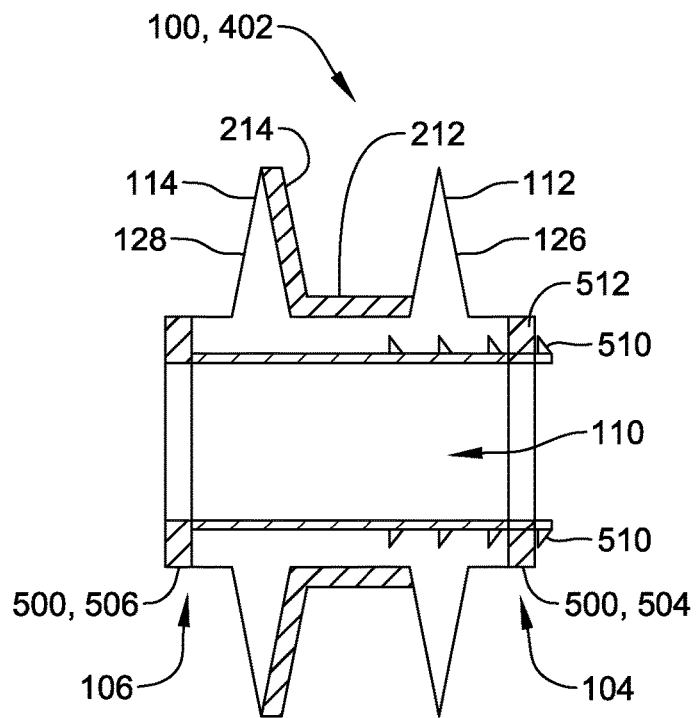
FIG. 7 is a sectional view of the implant and locking mechanism of FIG. 5, showing the implant in the expanded configuration of FIG. 4.

FIG. 5 is a perspective view of implant 100 coupled to opposing end caps 504 and 506 that cooperate to form a first exemplary embodiment of a locking mechanism, designated locking mechanism 500. FIG. 6 is a sectional view of implant 100 and locking mechanism 500, showing implant 100 in delivery configuration 102, and FIG. 7 is a sectional view of implant 100 and locking mechanism 500, in expanded configuration 402. With reference to FIGS. 1-7, a proximal end cap 504 is coupled to proximal end 104 of body 108, and a distal end cap 506 is coupled to distal end 106. Each of end caps 504 and 506 has a generally annular shape, such that implant lumen 110 is at most only partially obstructed at proximal end 104 and distal end 106. For example, end caps 504 and 506 are sized to allow passage of a suitable portion of a delivery device, such as but not limited to inner tube 1610 and hypo tube 1700 (shown in FIG. 16), through implant lumen 110 and end caps 504 and 506.

In the exemplary embodiment, locking mechanism 500 includes at least two legs 508 that each extend from distal end cap 506 towards proximal end cap 504. Each leg 508 is resilient and includes at least one tooth 510 configured to slide past and engage a lip 512 of proximal end cap 504 when implant 100 is transitioned from delivery configuration 102 to expanded configuration 402. For example, in the exemplary embodiment, each tooth 510 includes an inclined first surface 514 configured to facilitate resiliently sliding past lip 512 when implant 100 is transitioned from delivery configuration 102 to expanded configuration 402, and an opposite radially extending second surface 516 configured to engage lip 512 and inhibit implant 100 from transitioning back from expanded configuration 402 to delivery configuration 102. A length of legs 508 is selected to facilitate engagement of teeth 510 with lip 512 when implant 100 is in expanded configuration 402. In alternative embodiments, legs 508, teeth 510, and lip 512 have any suitable configuration that enables locking mechanism 500 to function as described herein.

Although legs 508 each extend from distal end cap 506 and engage lip 512 of proximal end cap 504 in the exemplary embodiment, it should be understood that in alternative embodiments, at least one leg 508 extends from proximal end cap 504 and engages a lip of distal end cap 506.

In alternative embodiments, implant 100 does not include locking mechanism 500.

Figure 8:
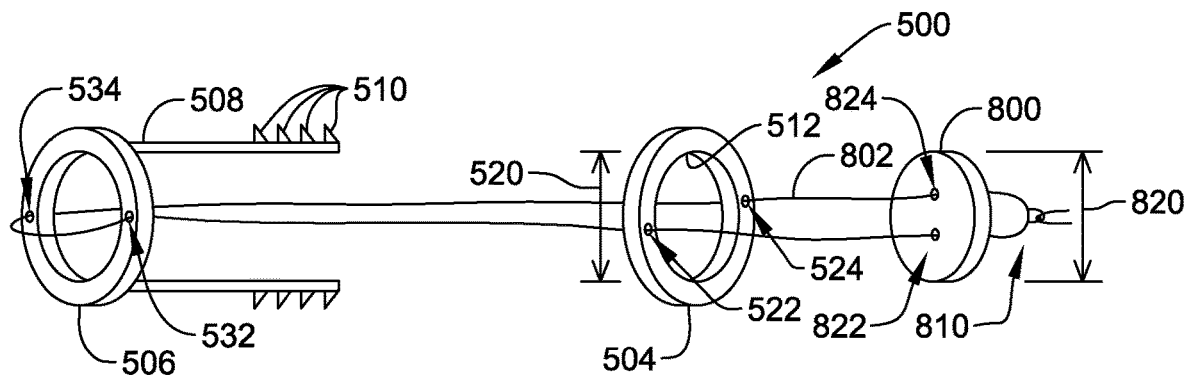
FIG. 8 is an exploded view of the locking mechanism of FIG. 5.

FIG. 8 is an exploded view of locking mechanism 500. In the exemplary embodiment, locking mechanism 500 includes a plug 800 positionable to facilitate sealing implant lumen 110 after implant 100 in expanded configuration 402 is positioned at the puncture site. Plug 800 is generally disk shaped and includes a first opening 822 and an opposite second opening 824 extending longitudinally therethrough. Similarly, first end cap 504 includes a first opening 522 and an opposite second opening 524 extending longitudinally therethrough, and second end cap 506 includes a first opening 532 and an opposite second opening 534 extending longitudinally therethrough.

A suture 802, formed for example from a bioabsorbable material, is threaded in the distal direction through first opening 822 of plug 800, first opening 522 of end cap 504, and first opening 532 of second end cap 506, and then around and back in the proximal direction through second opening 534 of second end cap 506, second opening 524 of end cap 504, and second opening 824 of plug 800. In certain embodiments, locking mechanism has two legs 508 circumferentially spaced approximately 180 degrees apart, and openings 822, 522, and 532 are each positioned circumferentially approximately ninety degrees from each of legs 508, such that opposing openings 824, 524, and 534 also are each positioned circumferentially approximately ninety degrees from each of legs 508. In alternative embodiments, locking mechanism has any suitable number of legs 508 spaced in any suitable fashion, and openings 822, 522, 532, 824, 524, and 824 are spaced in any suitable fashion, that enables plug 800 to function as described herein.

In the exemplary embodiment, a diameter 820 of plug 800 is slightly larger than an inner annular diameter 520 of first end cap 504. In alternative embodiments, diameter 820 is any suitable diameter that enables plug 800 to function as described herein. In the exemplary embodiment, a sliding knot 810 is formed in suture 802 proximal to plug 800. After implant 100 has been deployed and delivery device 1600 (shown in FIG. 3) has been extracted from the puncture site, sliding knot 810 is advanced distally, for example using a suitable a knot pusher (not shown), such that plug 800 is advanced distally along suture 802 into sealing contact with the annular opening of first end cap 504. In certain embodiments, plug 800 thus facilitates sealing implant lumen 110. Additionally or alternatively, in some embodiments, sliding knot 810 is advanced distally such that suture 802 secures or locks implant 100 in expanded configuration 402 (shown in FIG. 4), for example redundantly with or in the absence of locking mechanism 500. In alternative embodiments, implant lumen 110 is sealed in any suitable fashion that enables implant 100 to function as described herein.

Figure 9:
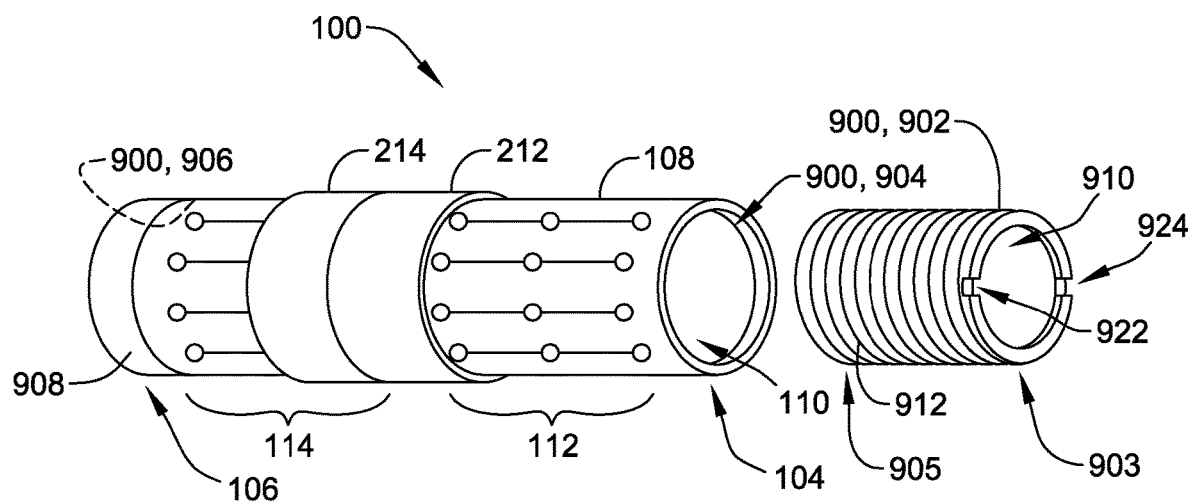
FIG. 9 is a perspective view of the implant of FIG. 1 that includes a screw and interior threads that cooperate to form a second exemplary embodiment of an implant locking mechanism.
Figure 10:
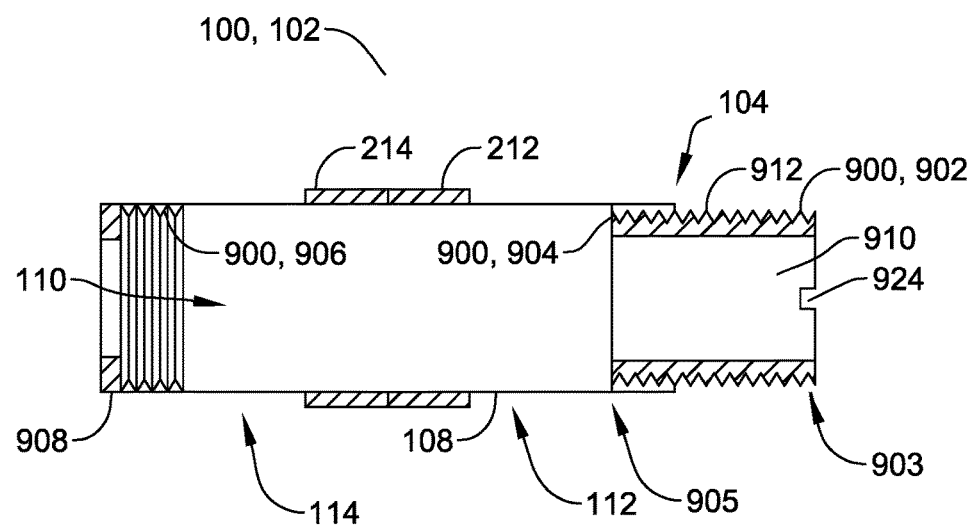
FIG. 10 is a sectional view of the implant and locking mechanism of FIG. 9, showing the implant in the delivery configuration of FIG. 1.
Figure 11:
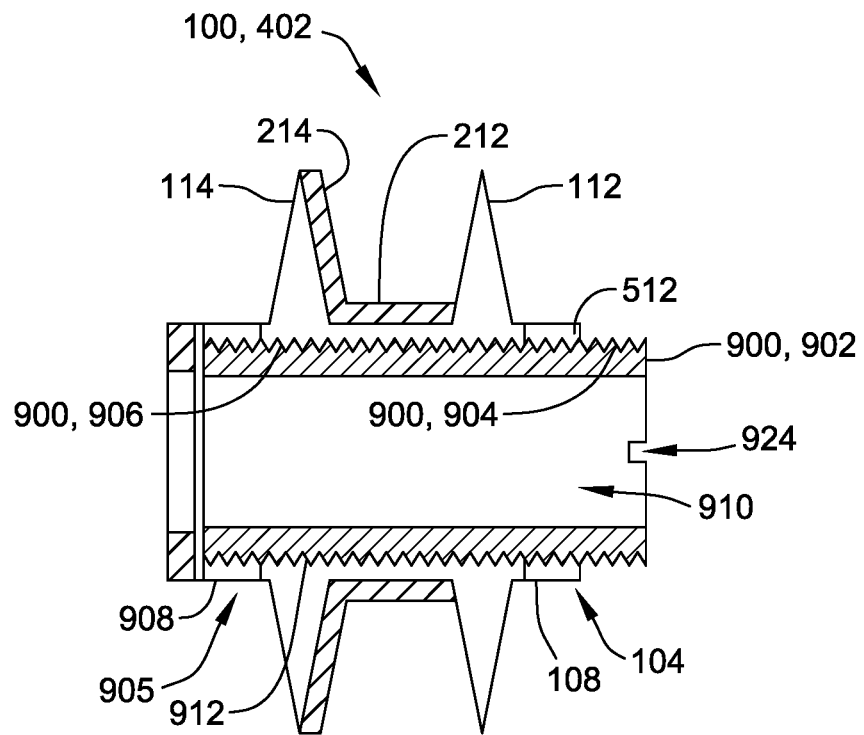
FIG. 11 is a sectional view of the implant and locking mechanism of FIG. 9, showing the implant in the expanded configuration of FIG. 4.

FIG. 9 is a perspective view of implant 100 that includes a screw 902 and interior threads 904 and 906 that cooperate to form a second exemplary embodiment of a locking mechanism, designated locking mechanism 900. FIG. 10 is a sectional view of implant 100 including locking mechanism 900 in delivery configuration 102, and FIG. 11 is a sectional view of implant 100, including locking mechanism 900, in expanded configuration 402.

With reference to FIGS. 1-4 and 9-11, in the exemplary embodiment, screw 902 is generally tubular shaped and defines a lumen 910 extending longitudinally therethrough. In the exemplary embodiment, screw 902 is formed from a bioabsorbable material as discussed above. An exterior thread 912 is disposed on an outer surface of screw 902. In alternative embodiments, screw 902 has any suitable shape that enables locking mechanism 900 to function as described herein.

Further in the exemplary embodiment, proximal interior thread 904 is defined on an inner surface of generally tubular body 108 between proximal end 104 and first expandable section 112, and distal interior thread 906 is defined on the inner surface of generally tubular body 108 between distal end 106 and second expandable section 114. Interior threads 904 and 906 are complementary to exterior thread 912 of screw 902, such that screw 902 is threadably engageable within body 108.

In certain embodiments, to operate locking mechanism 900, exterior thread 912 at a distal end 905 of screw 902 is initially pushed against and/or rotated slightly into proximal interior thread 904, as shown in FIG. 10. Distal end 106 of body 108 is held stationary by a suitable delivery device, as will be described herein, and screw 902 is then pushed in the distal direction, without rotation, such that screw 902 exerts a compressive force on body 108. In response, body 108 transitions from delivery configuration 102 to expanded configuration 402. While a suitable compressive force is maintained to retain body 108 in expanded configuration 402, screw 902 is rotated such that exterior thread 912 advances distally along proximal interior thread 904 in threaded cooperation, and then engages and advances distally along distal interior thread 906 in threaded cooperation. Exterior thread 912 of screw 902 engaged with proximal interior thread 904 and distal interior thread 906 facilitates locking implant 100 in expanded configuration 402, even after removal of the initial compressive force, as shown in FIG. 11. In alternative embodiments, locking mechanism 900 is operable in any suitable fashion that enables implant 100 to function as described herein.

In the exemplary embodiment, screw lumen 910 is sized such that implant lumen 110 is at most only partially obstructed. For example, screw lumen 910 is sized to allow passage of a suitable portion of a delivery device, such as but not limited to inner tube 1610 and hypo tube 1700 (shown in FIG. 16), therethrough.

In certain embodiments, locking mechanism 900 further includes a plug (not shown), similar to plug 800 described above, positionable to facilitate sealing implant lumen 110 after implant 100 in expanded configuration 402 is positioned at the puncture site.

Figure 12:
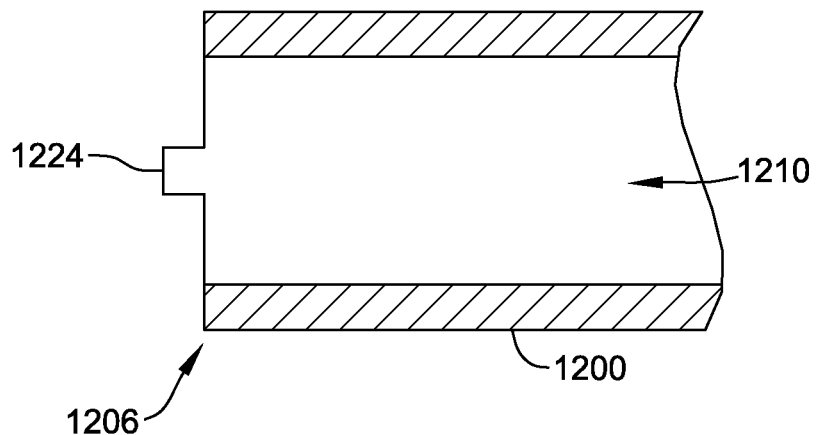
FIG. 12 is a sectional view of a driver that may be used to operate the locking mechanism of FIG. 9.

FIG. 12 is a sectional view of a driver 1200 that may be used to operate locking mechanism 900 as described above. With reference to FIGS. 9-12, in the exemplary embodiment, a face of a proximal end 903 of screw 902 includes a pair of aligned opposing slots 922 and 924 defined therein. A face of a distal end 1206 of driver 1200 includes a pair of aligned opposing projections, including projection 1224 and an aligned projection not visible in the illustrated section view, that are sized to be received respectively by slots 924 and 922 when distal end 1206 of driver 1200 is positioned against proximal end 903 of screw 902 and suitably rotationally aligned. Driver 1200 is thus operable alternatively to push screw 902 without rotation in the distal direction, and to rotate screw 902 to advance the threaded coupling of locking mechanism 900, as described above.

In the exemplary embodiment, driver 1200 is generally tubular shaped and defines a lumen 1210 extending longitudinally therethrough. Driver lumen 1210 is sized such that implant lumen 110 is at most only partially obstructed. For example, driver lumen 1210 is sized to allow passage of a suitable portion of a delivery device, such as but not limited to inner tube 1610 and hypo tube 1700 (shown in FIG. 16), therethrough.

In alternative embodiments, any suitable driver is used to operate screw 902.

Also in the exemplary embodiment, implant 100 includes a distal end cap 908 coupled to distal end 106 of body 108. Distal end cap 908 is generally annular in shape and extends radially inward to a sufficient extent such that distal end cap 908 obstructs advancement of distal end 905 of screw past distal end 106 of body 108. Thus, distal end cap 908 functions as a stop for screw 902.

In the exemplary embodiment, the annular opening of end cap 908 is sized such that implant lumen 110 is at most only partially obstructed at distal end 106. For example, end cap 908 is sized to allow passage of a suitable portion of a delivery device, such as but not limited to inner tube 1610 and hypo tube 1700 (shown in FIG. 16), therethrough through implant lumen 110 and end cap 908.

In alternative embodiments, implant 100 does not include end cap 908. For example, implant 100 includes another suitable stop for screw 902.

Figure 13:
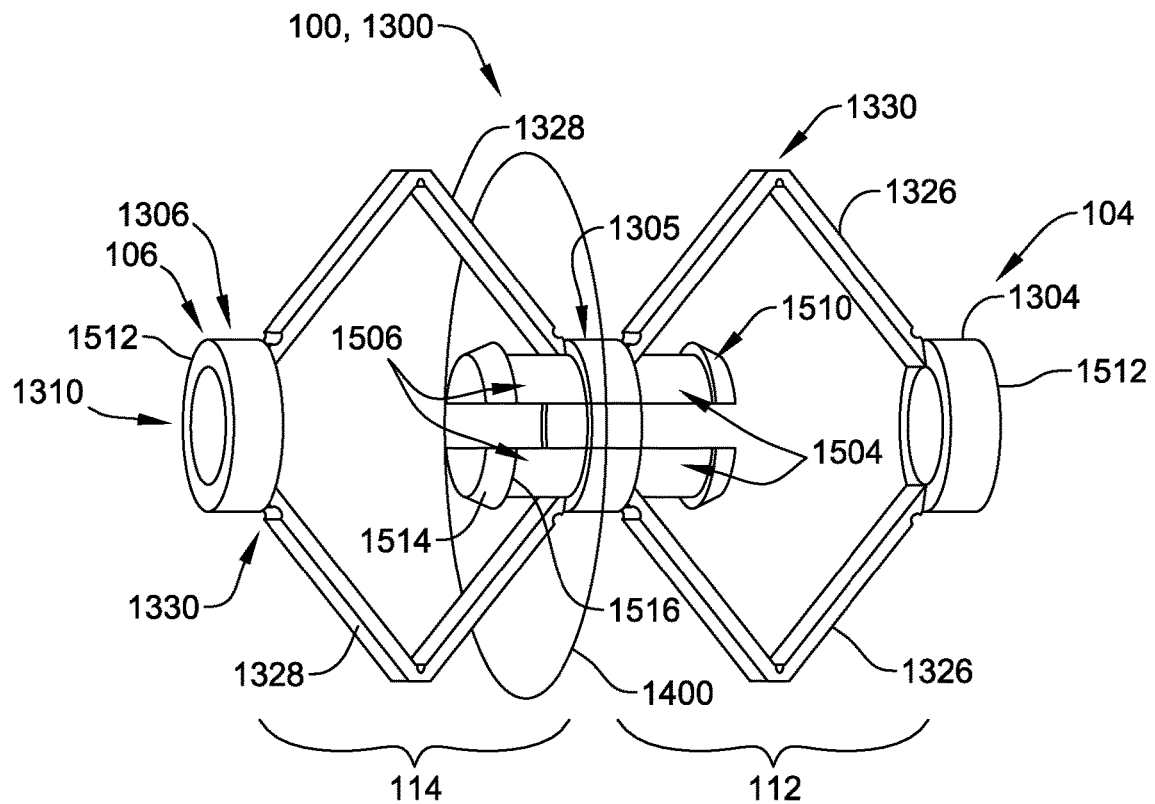
FIG. 13 is a perspective view of a second exemplary embodiment of an implant.
Figure 14:
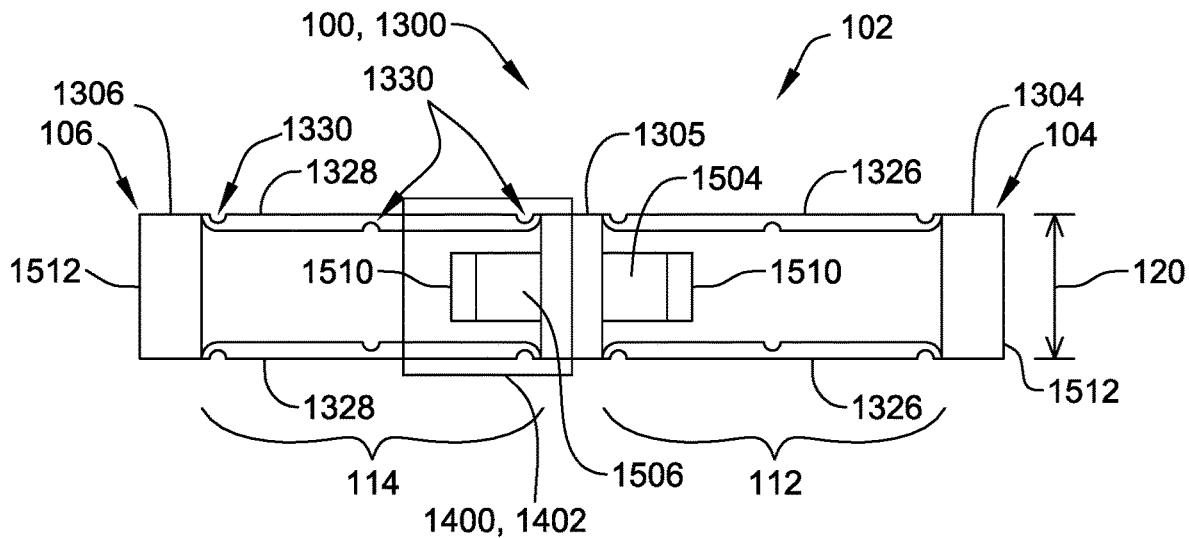
FIG. 14 is a side view of the implant of FIG. 13 in a delivery configuration.
Figure 15:
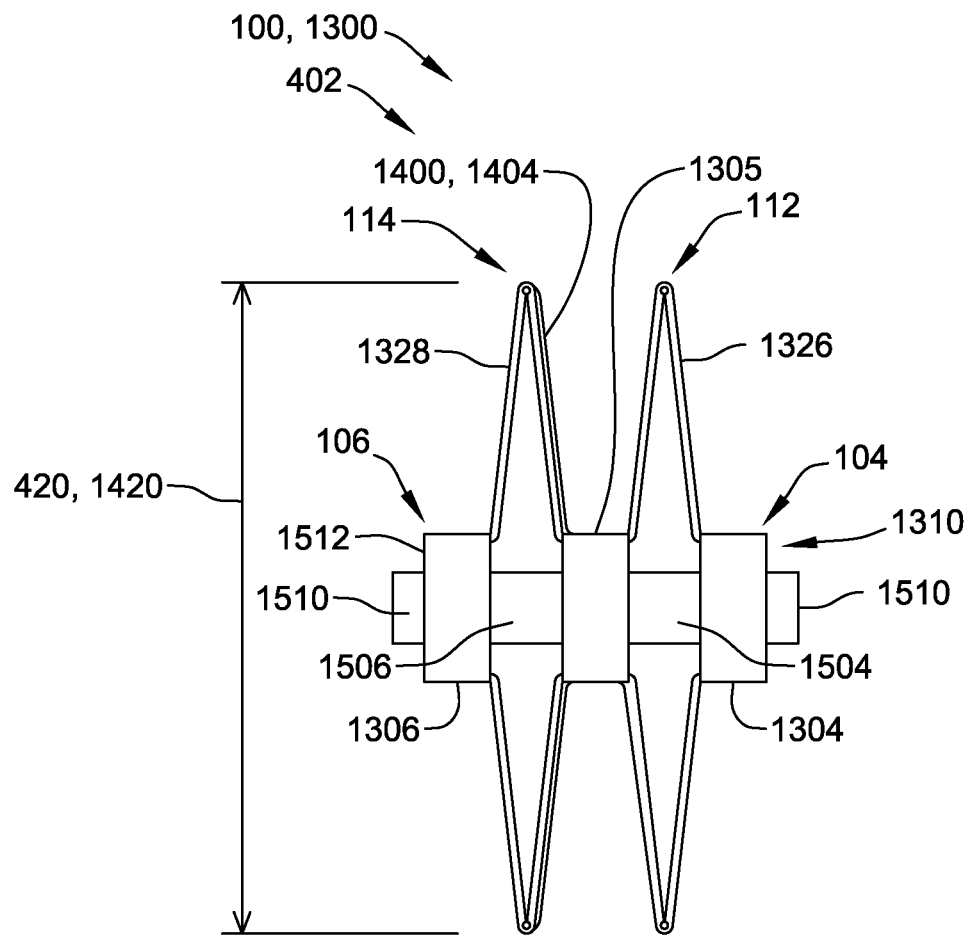
FIG. 15 is a side view of the implant of FIG. 13 in an expanded configuration.

FIG. 13 is a perspective view of a second exemplary embodiment of implant 100, designated implant 1300, for facilitating hemostasis at a puncture site of an artery wall. FIG. 14 is a side view of implant 1300 in delivery configuration 102. FIG. 15 is a side view of implant 1300 in expanded configuration 402.

In the exemplary embodiment, implant 1300 includes a proximal ring 1304 at proximal end 104 and a distal ring 1306 at distal end 106. A middle ring 1305 is oriented coaxially with proximal ring 1304 and distal ring 1306 along the longitudinal direction, and each of rings 1304, 1305, and 1306 defines a lumen 1310 extending longitudinally therethrough. In certain embodiments, implant lumen 1310 is sized to allow passage of a suitable guidewire therethrough. In the exemplary embodiment, implant 1300 is formed from a bioabsorbable polymer as described above. In alternative embodiments, implant 1300 is formed from any suitable material that enables implant 1300 to function as described herein.

As described above, implant 1300 in delivery configuration 102 is sized for insertion through a puncture site in an artery into a lumen of the artery (shown for example in FIG. 29). For example, in certain embodiments, implant 1300 is again sized for use at a puncture site associated with a sheath having a diameter in a range of about 9 Fr to about 24 Fr, such that delivery diameter 120 of implant 1300 is in a range of about 3 millimeters to about 8 millimeters. In alternative embodiments, implant 1300 is sized for use at a puncture site associated with a sheath having any suitable diameter, and delivery diameter 120 of implant 1300 is any suitable corresponding diameter for insertion through the puncture site.

A first plurality of expandable struts 1326 coupled between proximal ring 1304 and middle ring 1305 define first expandable section 112, and a second plurality of expandable struts 1328 coupled between middle ring 1305 and distal ring 1306 define second expandable section 114. In the exemplary embodiment, first plurality of expandable struts 1326 includes two struts 1326 spaced 180 degrees apart along a circumference of implant 1300, and second plurality of expandable struts 1328 also includes two struts 1328 spaced 180 degrees apart along the circumference of implant 1300. In alternative embodiments, each of first plurality of expandable struts 1326 and second plurality of expandable struts 1328 includes any suitable number of struts spaced circumferentially in any suitable fashion that enables implant 1300 to function as described herein.

As described above, each of first expandable section 112 and second expandable section 114 is selectively expandable radially outward from equal to, or less than, delivery diameter 120 to expanded diameter 420. More specifically, expandable struts 1326 and 1328 are configured to bulge radially outward in response to a compressive force applied longitudinally to implant 1300, thereby expanding sections 112 and 114 to expanded diameter 420. In alternative embodiments, each of first expandable section 112 and second expandable section 114 is configured to selectively expand radially outward in any suitable fashion that enables implant 1300 to function as described herein. Expanded diameter 420 is again sized to be greater than the diameter of the opening in the wall of the artery at the puncture site, such that after implant 1300 in delivery configuration 102 is deployed longitudinally into the puncture opening, first expandable section 112 and second expandable section 114 are selectively expandable on opposing sides of the artery wall to restrict further longitudinal movement of implant 1300 and thereby facilitate retaining implant 1300 within the puncture opening, as will be described herein.

In the exemplary embodiment, stress relief regions 1330 are defined in each opposing end of each expandable strut 1326 and 1328, and at approximately the middle of each expandable strut 1326 and 1328. Stress relief regions 1330 facilitate articulation of expandable struts 1326 and 1328 by creating weak regions proximate the ends and middle of each strut 1326 and 1328, facilitating bending of struts 1326 and 1328 at the ends and middle in response to a compressive force. In the exemplary embodiment, stress relief regions 1330 are formed from generally semi-circular depressions extending radially into the respective strut. In alternative embodiments, stress relief regions 1330 are formed in any suitable fashion. In other alternative embodiments, implant 1300 does not include stress relief regions 1330.

In the exemplary embodiment, a skirt 1400, similar in many respects to skirt 200 described above, is coupled to implant 1300. In the exemplary embodiment, skirt 1400 is coupled to a proximal portion of at least two of second expandable struts 1328. In alternative embodiments, skirt 1400 is coupled to any suitable portion of implant 1300 that enables skirt 1400 to function as described herein.

In the exemplary embodiment, skirt 1400 is formed from a bioabsorbable material as discussed above. Although skirt 1400 is illustrated as formed from a translucent material in FIGS. 13-15, in alternative embodiments, skirt 1400 is formed from a material that is other than translucent.

More specifically, skirt 1400 is illustrated in a delivery configuration 1402 in FIG. 14, and in an expanded configuration 1404 in FIG. 15. In delivery configuration 1402, skirt 1400 has a generally tubular shape with pleats and is concentrically adjacent a proximal portion of second expandable section 114. In expanded configuration 1404, skirt 1400 is flared radially outward adjacent the proximal portions of expandable struts 1328, generally into a disk shape normal to the longitudinal direction of implant 1300 and having a diameter 1420. Diameter 1420 is approximately equal to diameter 420 of second expandable section 114, such that skirt 1400 again facilitates occluding blood flow from the lumen of the artery through the puncture site, such as through gaps between struts 1328 in expanded configuration 402, when implant 1300 is positioned within the puncture opening. For example, but not by way of limitation, as discussed above with respect to skirt 200, skirt 1400 is formed from a flexible membrane that enables skirt 1400 to transition from delivery configuration 1402 to expanded configuration 1404. Additionally or alternatively, implant 1300 includes a similar skirt (not shown) configured for positioning adjacent first expandable section 112 to further facilitate occluding blood flow from the lumen of the artery through the puncture site. In alternative embodiments, skirt 1400 has any suitable structure that enables skirt 1400 to function as described herein.

In alternative embodiments, implant 1300 does not include skirt 1400.

In the exemplary embodiment, implant 1300 also includes a third exemplary embodiment of a locking mechanism, designated locking mechanism 1500. Locking mechanism 1500 includes a first plurality of resilient flanges 1504 extending from middle ring 1305 towards proximal ring 1304, and a second plurality of resilient flanges 1506 extending from middle ring 1305 towards distal ring 1306. In the exemplary embodiment, first plurality of resilient flanges 1504 includes two flanges 1504 spaced 180 degrees apart along a circumference of implant 1300, and second plurality of resilient flanges 1506 also includes two flanges 1506 spaced 180 degrees apart along the circumference of implant 1300. Also in the exemplary embodiment, each flange 1504 is spaced 90 degrees circumferentially from each expandable strut 1326, and each flange 1506 is spaced 90 degrees circumferentially from each expandable strut 1328, which in certain embodiments facilitates a reduced potential for interference between the respective flanges and struts during transition of implant 1300 from delivery configuration 102 to expanded configuration 402. In alternative embodiments, each of first plurality of resilient flanges 1504 and second plurality of resilient flanges 1506 includes any suitable number of flanges spaced circumferentially in any suitable fashion that enables implant 1300 to function as described herein.

In the exemplary embodiment, each resilient flange 1504 and 1506 includes a tooth 1510 configured to slide past and engage a lip 1512 of proximal ring 1304 and distal ring 1306, respectively, when implant 1300 is transitioned from delivery configuration 102 to expanded configuration 402. For example, in the exemplary embodiment, each tooth 1510 includes an inclined first surface 1514 configured to facilitate resiliently sliding past lip 1512 when implant 1300 is transitioned from delivery configuration 102 to expanded configuration 402, and an opposite radially extending second surface 1516 configured to engage lip 1512 and inhibit implant 1300 from transitioning back from expanded configuration 402 to delivery configuration 102. A length of flanges 1504 and 1506 is selected to facilitate engagement of teeth 1510 with lip 1512 when implant 1300 is in expanded configuration 402. In alternative embodiments, flanges 1504 and 1506, teeth 1510, and lips 1512 have any suitable configuration that enables locking mechanism 1500 to function as described herein.

Although in the exemplary embodiment flanges 1504 and 1506 each extend from middle ring 1305 and engage lip 1512 of proximal ring 1304 and distal ring 1306, respectively, it should be understood that in alternative embodiments, at least one flange 1504 or 1506 extends from proximal ring 1304 or distal ring 1306, respectively, and engages a lip of middle ring 1305.

In certain embodiments, locking mechanism 1500 further includes a plug (not shown), similar to plug 800 described above, positionable to facilitate sealing implant lumen 110 after implant 100 in expanded configuration 402 is positioned at the puncture site.

In alternative embodiments, implant 100 does not include locking mechanism 1500.

Figure 16:
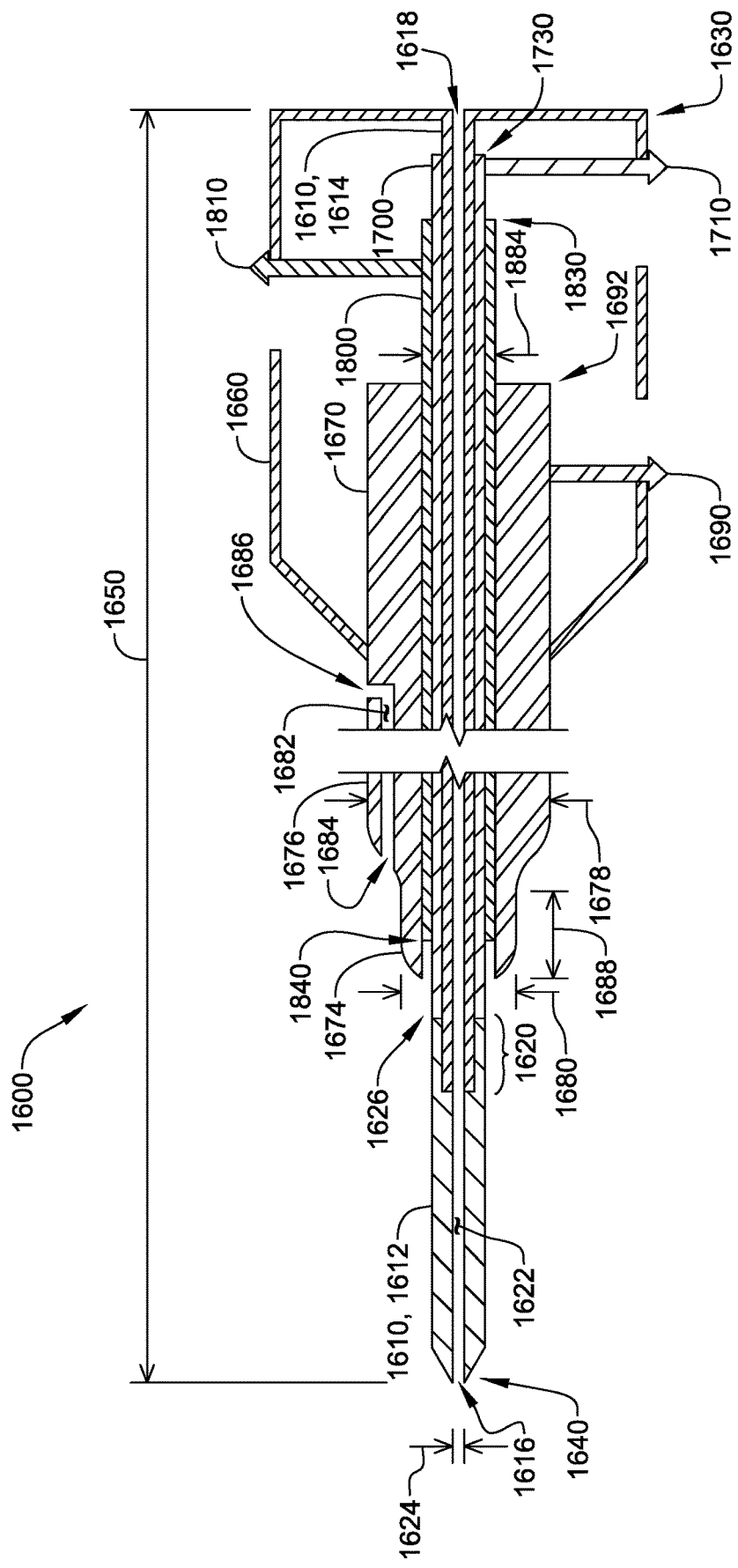
FIG. 16 is a section view of an exemplary embodiment of a delivery device for deploying an implant, such as any of the implants shown in FIGS. 1-11 and 13-15.
Figure 17:
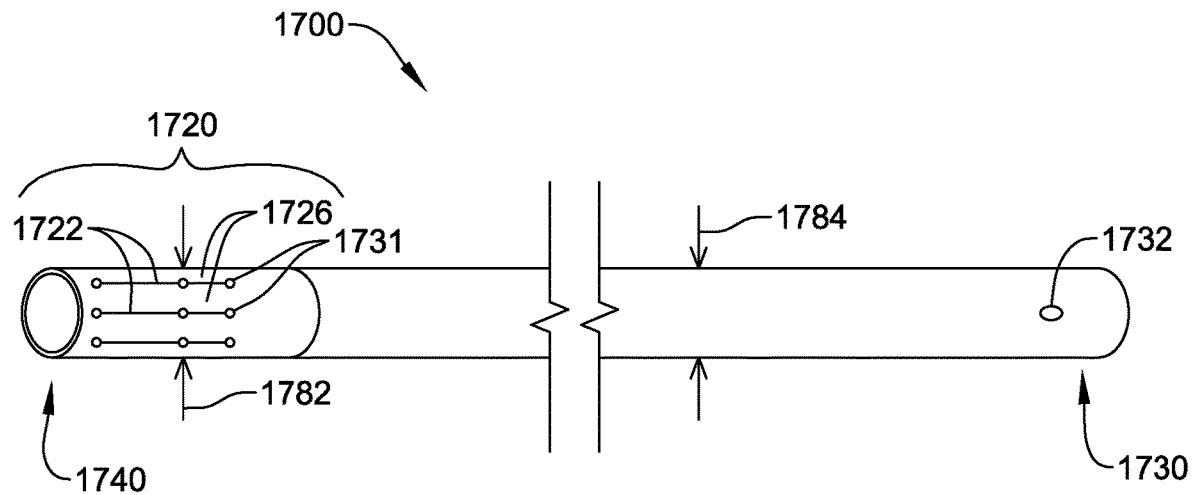
FIG. 17 is a perspective view of an exemplary embodiment of a hypo tube that may be used as part of the delivery device of FIG. 16.
Figure 18:
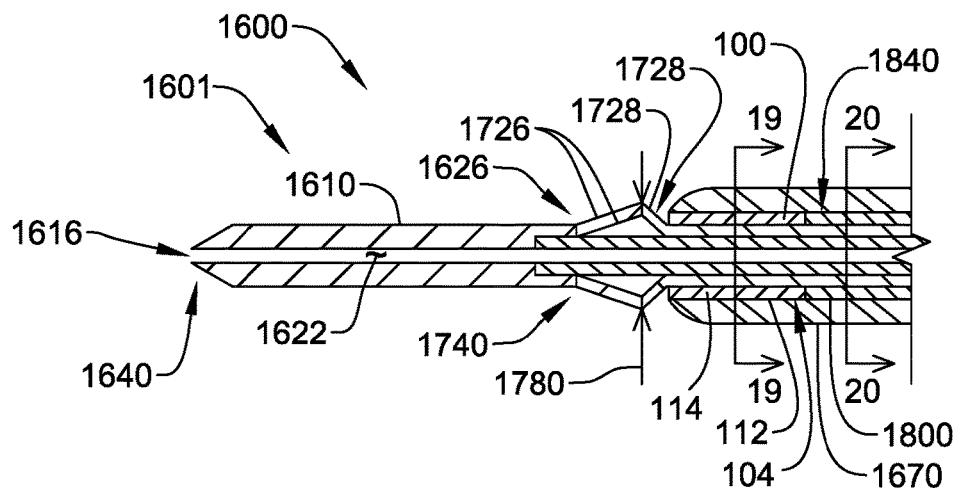
FIG. 18 is a section view of an embodiment of a system to facilitate sealing a puncture of a vessel, the system including the delivery device of FIG. 16 and any of the implants shown in FIGS. 1-11 and 13-15.
Figure 19:
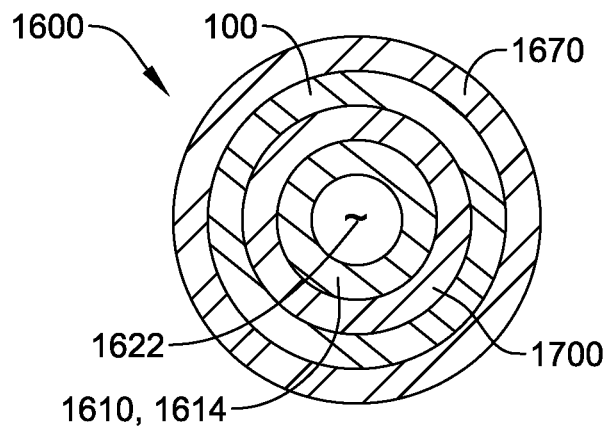
FIG. 19 is a section view of the system of FIG. 18 along lines 19-19 shown in FIG. 18.
Figure 20:
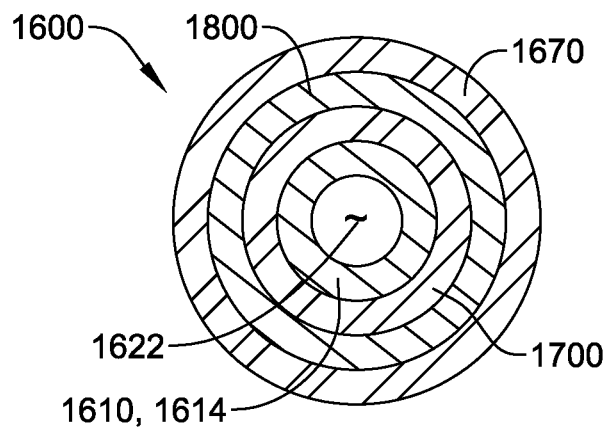
FIG. 20 is a section view of the system of FIG. 18 along lines 20-20 shown in FIG. 18.

FIG. 16 is a section view of an exemplary embodiment of a delivery device 1600 for deploying implant 100 at a puncture site of an artery. FIG. 17 is a perspective view of an exemplary embodiment of hypo tube 1700 that may be used as part of delivery device 1600. FIG. 18 is a section view of an embodiment of a system 1601 to facilitate sealing a puncture of a vessel, the system including delivery device 1600 and implant 100. FIG. 19 is a section view of system 1601 along lines 19-19 shown in FIG. 18, and FIG. 20 is a section view of system 1601 along lines 20-20 shown in FIG. 18.

With reference to FIGS. 16-20, in the exemplary embodiment, delivery device 1600 has a proximal end 1630, a distal end 1640, and a length 1650. In the exemplary embodiment, length 1650 is at least approximately 5 inches (in.). More particularly, length 1650 is between approximately 8 in. and approximately 12 in. Alternatively, delivery device 1600 has any suitable length that enables delivery device 1600 to function as described herein.

Delivery device 1600 includes a first or inner tube 1610 coupled to a housing 1660. In the exemplary embodiment, inner tube 1610 extends from proximal end 1630 to distal end 1640, and inner tube 1610 is tapered at distal end 1640 to facilitate traversing through subcutaneous tissue and into a lumen of the vessel. In alternative embodiments, inner tube 1610 extends to any suitable extent, and has any suitable shape at distal end 1640, that enables delivery device 1600 to function as described herein.

In the exemplary embodiment, inner tube 1610 includes a distal portion 1612 and a proximal portion 1614 coupled together at a coupling 1620. Distal portion 1612 and proximal portion 1614 are disposed coaxially and cooperate to define a first or inner lumen 1622 within inner tube 1610 and extending therethrough. In the exemplary embodiment, distal portion 1612 defines a distal opening 1616 at distal end 1640, and proximal portion 1614 is coupled to housing 1660 and extends therethrough to a proximal opening 1618, such that distal opening 1616 and proximal opening 1618 are in flow communication with inner lumen 1622. Inner lumen 1622 is sized to allow passage of a guidewire (not shown) therethrough. For example, but not by way of limitation, inner lumen 1622 has a diameter 1624 equal to 0.038 inches to allow for passage of a 0.035 inch diameter guidewire.

In the exemplary embodiment, coupling 1620 is defined by an interference fit between distal portion 1612 and proximal portion 1614. More specifically, an inner diameter of distal portion 1612 proximate a proximal end 1626 of distal portion 1612 is matched to an outer diameter of a distal end of proximal portion 1614, such that the proximal end of distal portion 1612 fits coaxially around the distal end of proximal portion 1614 in the interference fit. In the exemplary embodiment, proximal end 1626 of distal portion 1612 defines a circumferentially extending step that projects radially outward, relative to an outer wall of proximal portion 1614, at coupling 1620.

Alternatively, inner tube 1610 includes any suitable number of portions, and/or the portions are coupled in any suitable configuration and/or using any suitable mechanism that enables inner tube 1610 to function as described herein.

In the exemplary embodiment, delivery device 1600 also includes hypo tube 1700 circumscribing at least a portion of inner tube 1610. More specifically, in the exemplary embodiment, hypo tube 1700 is sized to fit coaxially around proximal portion 1614 of inner tube 1610. Hypo tube 1700 extends longitudinally from a proximal end 1730 to a distal end 1740. Proximal end 1730 is disposed within housing 1660. A hypo tube actuator 1710 accessible on housing 1660 is operable to move hypo tube 1700 distally and proximally relative to inner tube 1610. For example, but not by way of limitation, a connector 1732 disposed proximate proximal end 1730 is configured to cooperate with hypo tube actuator 1710. In certain embodiments, connector 1732 includes a pair of opposing pegs extending radially outward from hypo tube 1700 and configured to be received in a slot (not shown) defined in actuator 1710.

An outer diameter 1784 of hypo tube 1700 is selected to enable implant 100 (shown in any of FIGS. 1-11 and 13-15) to be positioned coaxially around an outer surface of hypo tube 1700. Hypo tube 1700 includes an expandable portion 1720 proximate distal end 1740 operable to selectively retain implant 100 longitudinally on delivery device 1600 and facilitate deployment of implant 100 from delivery device 1600. Expandable portion 1720 is selectively actuatable between a neutral configuration (shown in FIG. 17) and a stopper configuration (shown in FIG. 18). In the stopper configuration, expandable portion 1720 has a first diameter 1780, and in the neutral configuration, expandable portion 1720 has a second diameter 1782 that is less than first diameter 1780. First diameter 1780 is greater than inner diameter 121 of implant 100, such that expandable portion 1720 in the stopper configuration forms a retaining lip 1728 adjacent a distal end of implant 100 that is configured to retain implant 100 longitudinally on delivery device 1600. Second diameter 1782 is less than inner diameter 121 of implant 100, such that expandable portion 1720 in the neutral configuration is configured to facilitate releasing implant 100 from distal end 1640 of inner tube 1610. For example, but not by way of limitation, second diameter 1782 is approximately equal to outer diameter 1784 of hypo tube 1700.

In the exemplary embodiment, expandable portion 1720 is implemented as a malecot defined by a plurality of longitudinally extending cuts 1722 defined in hypo tube 1700. More specifically, longitudinal cuts 1722 are spaced circumferentially about hypo tube 1700, and each cut 1722 extends radially therethrough hypo tube 1700. Each pair of circumferentially adjacent longitudinal cuts 1722 cooperates to define a respective one of a plurality of expandable struts 1726 therebetween. Expandable struts 1726 are configured to bulge radially outward in response to a compressive force applied longitudinally to hypo tube 1700, thereby expanding expandable portion 1720 to first diameter 1780, and to return to second diameter 1782 when the compressive force is removed. In alternative embodiments, expandable portion 1720 is configured to selectively actuate between first diameter 1780 and second diameter 1782 in any suitable fashion that enables hypo tube 1700 to function as described herein.

In the exemplary embodiment, stress relief regions 1731 are defined in hypo tube 1700 at each opposing end of each longitudinal cut 1722, and at approximately one-third of the length of each longitudinal cut 1722 from the respective proximal end of the longitudinal cut 1722. Stress relief regions 1731 facilitate articulation of expandable struts 1726 by creating weak regions in hypo tube 1700 proximate the ends and the one-third length position of each strut 1726, facilitating bending of struts 1726 at the ends and one-third length position in response to a compressive force. In certain embodiments, locating the central bending point of each strut 1726 at the one-third length position from the proximal end of strut 1726 causes expandable portion 1720 to form a steeper retaining lip 1728 adjacent a distal end of implant 100, as compared to a more distal central bending point, facilitating improved longitudinal retention of implant 100.

In the exemplary embodiment, stress relief regions 1731 are formed from generally circular cutouts extending radially therethrough hypo tube 1700. In alternative embodiments, stress relief regions 1731 are formed in any suitable fashion. In other alternative embodiments, hypo tube 1700 does not include stress relief regions 1731.

In the exemplary embodiment, expandable portion 1720 is formed from a material that provides a desired degree of deformability to struts 1726. For example, but not by way of limitation, expandable portion 1720 is fabricated from a Nitinol alloy. In alternative embodiments, expandable portion 1720 is fabricated from any suitable material that enables expandable portion 1720 to function as described herein. In certain embodiments, expandable portion 1720 is covered by a flexible sleeve (not shown) disposed circumferentially around expandable portion 1720 to facilitate preventing interaction between expandable struts 1726 and subcutaneous tissue. For example, but not by way of limitation, the sleeve is formed from an elastomer material. In alternative embodiments, expandable portion 1720 is not covered by a sleeve.

In the exemplary embodiment, distal end 1740 of hypo tube 1700 is coupled to proximal end 1626 of distal portion 1612 of inner tube 1610 such that longitudinal movement of distal end 1740 relative to inner tube 1610 is restricted. For example, but not by way of limitation, proximal end 1626 defines a circumferentially extending step that projects radially outward, and distal end 1740 is coupled against the step such that longitudinal movement of distal end 1740 is restricted. In alternative embodiments, distal end 1740 is fixed relative to inner tune 1610 in any suitable fashion that enables hypo tube 1700 to function as described herein.

Actuator 1710 is operable to advance proximal end 1730 of hypo tube 1700 in the distal direction. Because distal end 1740 of hypo tube 1700 is fixed as described above, operation of actuator 1710 exerts a compressive force on expandable portion 1720, causing expandable portion 1720 to expand to first diameter 1780. Actuator 1710 is further operable to retract proximal end 1730 back in the proximal direction, causing expandable portion 1720 to retract to second diameter 1782.

In alternative embodiments, delivery device 1600 does not include hypo tube 1700. For example, in some embodiments, as will be described herein, delivery device 1600 includes an alternative inner tube 2100 having an integral expandable portion 2120 (shown in FIGS. 21 and 22) in lieu of hypo tube 1700. For another example, in some embodiments, as will be described herein, delivery device 1600 includes an alternative hypo tube 2300, configured to selectively retain implant 100 via coupling to distal end cap 506, in lieu of hypo tube 1700.

In the exemplary embodiment, delivery device 1600 also includes a pusher 1800 that circumscribes at least a portion of hypo tube 1700 or, alternatively, at least a portion of hypo tube 2300 or, alternatively, at least a portion of inner tube 2100. Pusher 1800 extends longitudinally from a proximal end 1830 to a distal end 1840. Proximal end 1830 is disposed within housing 1660. Distal end 1840 is configured to exert a compressive force on proximal end 104 of implant 100 to selectively expand each of second expandable section 114 and first expandable section 112 of implant 100 into expanded configuration 402. More specifically, an outer diameter 1884 of pusher 1800 is selected to enable distal end 1840 of pusher 1800 to engage proximal end 104 of implant 100 when implant 100 is positioned adjacent distal end 1840.

In the exemplary embodiment shown in FIGS. 16-20, pusher 1800 is generally tubular and is sized to fit coaxially around hypo tube 1700. A pusher actuator 1810 accessible on housing 1660 is operable to move pusher 1800 distally and proximally relative to inner tube 1610. For example, but not by way of limitation, a connector (not shown) disposed proximate proximal end 1830 is configured to cooperate with pusher actuator 1810. In some embodiments, the connector includes a pair of opposing pegs extending radially outward from pusher 1800 and configured to be received in a slot (not shown) defined in actuator 1810.

In the exemplary embodiment actuator 1810 is operable to advance pusher 1800 in the distal direction, causing distal end 1840 of pusher 1800 to urge proximal end 104 of implant 100 in the distal direction. Because distal end 106 of implant 100 is retained by expandable portion 1720, operation of actuator 1810 exerts a compressive force on implant 100, which tends to cause each of second expandable section 114 and first expandable section 112 to expand into expanded configuration 402. Alternatively, pusher 1800 is stationary and hypo tube 2300 pulls implant 100 in the proximal direction, again causing distal end 1840 to exert a compressive force on proximal end 104 of implant 100, which tends to cause to each of second expandable section 114 and first expandable section 112 of implant 100 to expand into expanded configuration 402. In certain embodiments, actuator 1810 is further operable to retract proximal end 1830 back in the proximal direction.

In alternative embodiments, pusher 1800 and actuator 1810 are configured in any suitable fashion that enables delivery device 1600 to function as described herein.

In the exemplary embodiment, delivery device 1600 further includes outer tube 1670. Outer tube 1670 circumscribes at least a portion of inner tube 1610. More specifically, outer tube 1670 defines first lumen 1672 (shown in FIG. 3) extending longitudinally therethrough. First outer tube lumen 1672 is sized to receive therewithin at least a portion of pusher 1800, inner tube 1610, and hypo tube 1700, or alternatively pusher 1800, inner tube 1610, and hypo tube 2300, or alternatively inner tube 2100 and pusher 1800. First outer tube lumen 1672 also is sized to receive therewithin implant 100 positioned on any of hypo tube 1700, inner tube 2100, and hypo tube 2300.

In the exemplary embodiment, outer tube 1670 includes a distal portion 1674 and a proximal portion 1676. Proximal portion 1676 is coupled to housing 1660 and has an outer diameter 1678 selected to match an outer diameter of the procedural sheath used during the arterial procedure, that is, selected to match a diameter of the puncture opening in the arterial wall. As a result, outer tube 1670 occludes the puncture opening when outer tube 1670 is advanced through the artery wall. In alternative embodiments, proximal portion 1676 has any suitable size and configuration that enables delivery device 1600 to function as described herein.

In the exemplary embodiment, distal portion 1674 has an outer diameter 1680 that is significantly less than diameter 1678. Distal portion 1674 extends longitudinally over a length 1688 in a range of about 1 to about 3 centimeters and then smoothly transitions out to diameter 1678 of proximal portion 1676. In some embodiments, the relatively smaller outer diameter 1680 of distal portion 1674 allows an inferior flap of the artery wall created by the arterial puncture to return toward the artery wall as delivery device 1600 is withdrawn from the puncture opening, as will be described herein, thus reducing a potential for interference between the inferior flap and implant 100. In alternative embodiments, each of proximal portion 1676 and distal potion 1674 has any suitable size and configuration that enables delivery device 1600 to function as described herein.

In the exemplary embodiment, outer tube 1670 includes a second lumen 1682 defined therein. Second outer tube lumen 1682 extends longitudinally from a distal opening 1684 proximate distal portion 1674 to a proximal opening 1686 located just distal to housing 1660. Second outer tube lumen 1682 is offset axially from first outer tube lumen 1672, such that each of distal opening 1684 and proximal opening 1686 extends through a side wall of outer tube 1670 into flow communication with second outer tube lumen 1682. In alternative embodiments, proximal opening 1686 is located within housing 1660, and housing 1660 includes a passage (not shown) in flow communication with proximal opening 1686 and a side opening (not shown) in flow communication with the passage. In certain embodiments, a fluid reflux from the artery through second outer tube lumen 1682 facilitates confirming proper positioning of delivery device 1600 relative to the artery wall for deployment of implant 100, as will be described herein. In alternative embodiments, second outer tube lumen 1682 has any suitable configuration that enables delivery device 1600 to function as described herein. In other alternative embodiments, outer tube 1670 does not include second outer tube lumen 1682.

In the exemplary embodiment, outer tube 1670 is retractable relative to inner tube 1610 to facilitate selective expansion of each of second expandable section 114 and first expandable section 112 of implant 100 into expanded configuration 402, as will be described further herein. An outer tube actuator 1690 accessible on housing 1660 is operable to move outer tube 1670 proximally relative to inner tube 1610. For example, but not by way of limitation, a connector (not shown) disposed proximate a proximal end 1692 of outer tube 1670 is configured to cooperate with outer tube actuator 1690.

In certain embodiments, a portion of outer tube 1670 distal from housing 1660 is uncoupleable from housing 1660. For example, but not by way of limitation, outer tube 1670 includes a detachment mechanism 1698 (shown in FIG. 29), such as a luer lock, between proximal opening 1686 and the distal end of housing 1660, such that the portion of outer tube 1670 distal of the distal end of housing 1660 is uncoupleable from housing 1660. For example, the uncoupleable distal portion of outer tube 1670 is uncoupled from housing 1660 after implant 100 is deployed. In alternative embodiments, outer tube 1670 does not include detachment mechanism 1698.

Figure 21:
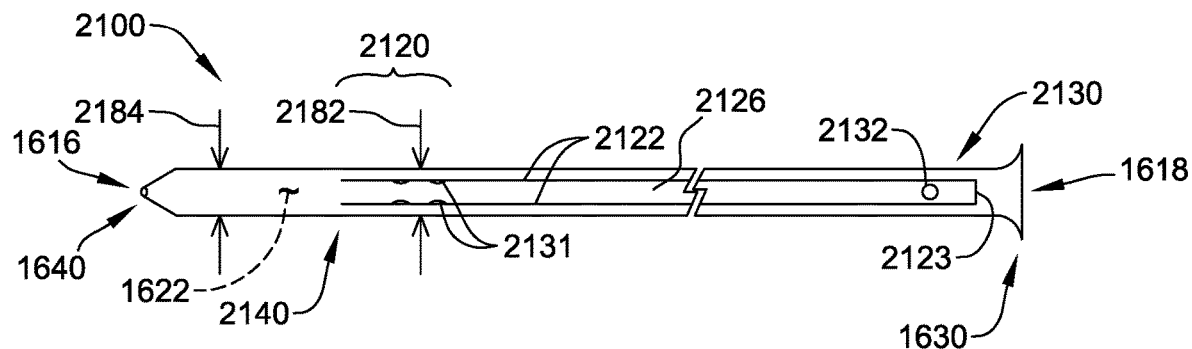
FIG. 21 is a perspective view of an exemplary embodiment of an alternative inner tube that may be used as part of the delivery device of FIG. 16, including an embodiment of an integral expandable portion.
Figure 22:
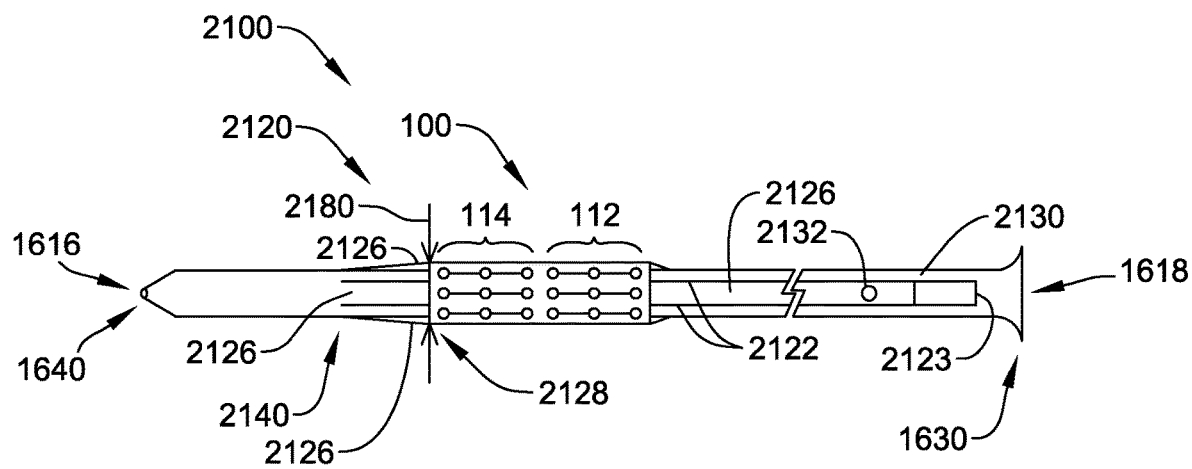
FIG. 22 is a perspective view of the inner tube of FIG. 21 having an implant, such as any of the implants shown in FIGS. 1-11 and 13-15, loaded thereon.

FIG. 21 is a perspective view of an exemplary embodiment of an alternative inner tube 2100 that includes integral expandable portion 2120. For example, inner tube 2100 may be used as part of delivery device 1600 as an alternative to inner tube 1610 and hypo tube 1700. FIG. 22 is a perspective view of inner tube 2100 having integral expandable portion 2120 and including implant 100 loaded thereon. Inner tube 2100 is similar in many respects to inner tube 1610 described above, and like features are numbered accordingly. However, in the exemplary embodiment, inner tube 2100 further includes a plurality of longitudinally extending cuts 2122 defined in inner tube 2100.

More specifically, longitudinal cuts 2122 are spaced circumferentially about inner tube 2100, and each cut 2122 extends radially therethrough inner tube 2100. Moreover, each cut 2122 extends from a proximal end 2130 to a distal end 2140. Alternating pairs of circumferentially adjacent longitudinal cuts 2122 are joined by a circumferentially extending cut 2123 to define a respective one of a plurality of expandable struts 2126 therebetween. No circumferential cuts are defined at distal end 2140, such that each strut 2126 is fixed relative to the distal portion of inner tube 2100. An outer diameter 2184 of inner tube 2100 proximal to distal end 2140 of struts 2126 is selected to enable implant 100 to be positioned coaxially around an outer surface of inner tube 2100.

A respective connector 2132 is disposed on each strut 2126 proximate proximal end 2130, and connectors 2132 are configured to cooperate with an actuator, such as actuator 1710 described above, to move proximal end 2130 of struts 2126 longitudinally forward and backward relative to inner tube 2100. For example, but not by way of limitation, connectors 2132 are pegs extending radially outward from inner tube 2100 and configured to be received in corresponding slots (not shown) defined in actuator 1710.

Expandable portion 2120 is defined adjacent distal end 2140 of struts 2126 and, similar to expandable portion 1720 described above, is selectively actuatable between a neutral configuration (shown in FIG. 21) and a stopper configuration (shown in FIG. 22). In the stopper configuration, expandable portion 2120 has a first diameter 2180, and in the neutral configuration, expandable portion 2120 has a second diameter 2182 that is less than first diameter 2180. First diameter 2180 is greater than inner diameter 121 of implant 100, such that expandable portion 2120 in the stopper configuration forms a retaining lip 2128 adjacent a distal end of implant 100 that is configured to retain implant 100 longitudinally on delivery device 1600. Second diameter 2182 is less than inner diameter 121 of implant 100, such that expandable portion 2120 in the neutral configuration is configured to facilitate releasing implant 100 from distal end 1640 of inner tube 1610. For example, but not by way of limitation, second diameter 2182 is approximately equal to outer diameter 2184 of inner tube 2100.

In the exemplary embodiment, expandable portion 2120 is implemented as a malecot. More specifically, expandable struts 2126 are configured to bulge radially outward proximate distal end 2140 in response to movement of proximal end 2130 of struts 2126 in the distal direction by the actuator, thereby expanding the malecot defining expandable portion 2120 to first diameter 2180, and to return to second diameter 2182 in response to movement of proximal end 2130 of struts 2126 back in the proximal direction by the actuator. In alternative embodiments, integral expandable portion 2120 is configured to selectively actuate between first diameter 2180 and second diameter 2182 in any suitable fashion that enables inner tube 2100 having integral expandable portion 2120 defined therein to function as described herein.

In the exemplary embodiment, stress relief regions 2131 are defined in each strut 2126 at a proximal end of expandable portion 2120, and at approximately one-third of the length of expandable portion 2120 from the respective proximal end of expandable portion 2120. Stress relief regions 2131 facilitate articulation of expandable struts 2126 by creating weak regions in strut 2126 proximate the end and the one-third length position of each strut 2126, facilitating bending of struts 2126 at the ends and one-third length position in response to a compressive force. In certain embodiments, locating the central bending point of each strut 2126 at the one-third length position from the proximal end of expandable portion 2120 causes expandable portion 2120 to form a steeper retaining lip 2128 adjacent a distal end of implant 100, as compared to a more distal central bending point, facilitating improved longitudinal retention of implant 100.

In the exemplary embodiment, stress relief regions 2131 are formed from generally semi-circular cutouts extending radially therethrough inner tube 2100. In alternative embodiments, stress relief regions 2131 are formed in any suitable fashion. In other alternative embodiments, expandable portion 2120 does not include stress relief regions 2131.

Delivery device 1600 including inner tube 2100 having integral expandable portion 2120 defined therein is operable similarly as described with respect to delivery device 1600 including inner tube 1610 and hypo tube 1700.

Figure 23:
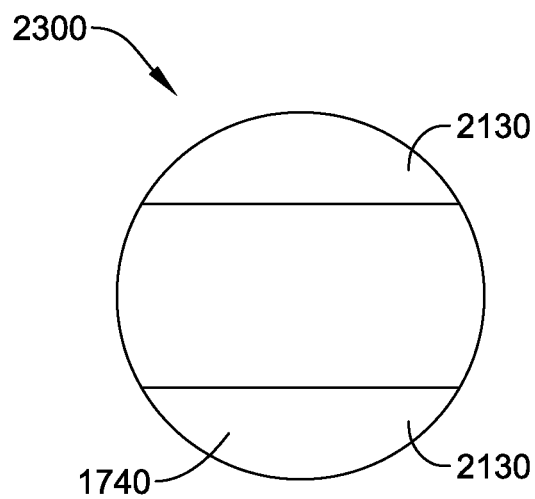
FIG. 23 is an end view of an exemplary embodiment of an alternative hypo tube that may be used as part of the delivery device of FIG. 16.
Figure 24:
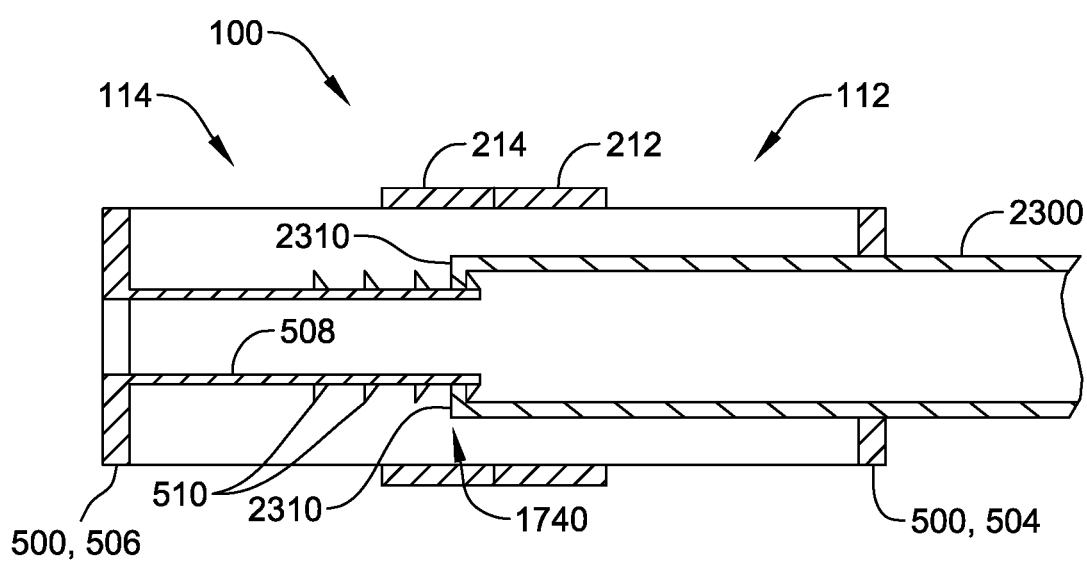
FIG. 24 is a section view of a distal portion of the hypo tube of FIG. 23 coupled to the implant of FIGS. 5-8)

FIG. 23 is an end view of an exemplary embodiment of an alternative hypo tube 2300 that may be used as part of delivery device 1600. For example, hypo tube 2300 may be used as part of delivery device 1600 including inner tube 1610, as an alternative to hypo tube 1700. FIG. 24 is a section view of a distal portion of hypo tube 2300 coupled to implant 100 having distal end cap 506 (shown in FIGS. 5-8). With reference to FIGS. 5-8, 16, 17, 23, and 24, hypo tube 2300 is configured to circumscribe at least a portion of inner tube 1610. Hypo tube 2300 is similar in many respects to hypo tube 1700 described above, and like features are numbered accordingly. However, in the exemplary embodiment, in lieu of expandable portion 1720 proximate distal end 1740, hypo tube 2300 includes at least two lips 2310 extending radially inward from distal end 1740.

Hypo tube 2300 is rotatable about its longitudinal axis between a first orientation, in which each lip 2310 is longitudinally aligned with a respective leg 508 of distal end cap 506 of implant 100, and a second orientation, in which each lip 2310 is not aligned with any of legs 508. For example, in the exemplary embodiment, legs 508 include two legs circumferentially spaced 180 degrees apart on end cap 506, lips 2310 correspondingly include two lips 2310 circumferentially spaced 180 degrees apart on distal end 1740 of hypo tube 2300, and the second orientation is 90 degrees from the first orientation. In the exemplary embodiment, actuator 1710 is operable to both rotate hypo tube 2300 between the first and second orientations, and to move hypo tube 2300 longitudinally. In alternative embodiments, delivery device includes any suitable actuator that enables hypo tube 2300 to function as described herein.

Lips 2310 are configured to engage legs 508 when hypo tube 2300 is in the first orientation, and to release legs 508 when hypo tube 2300 is in the second orientation. More specifically, lips 2310 are sized to enable at least one tooth 510 of each resilient leg 508 of distal end cap 506 to slide past and engage a respective lip 2310 when hypo tube 2300 is in the first rotational orientation and hypo tube is advanced distally, and to release the respective lip 2310 when hypo tube 2300 is rotated to the second orientation.

Moreover, when lips 2310 are engaged by respective teeth 510, in some embodiments, hypo tube 2300 is operable to pull distal end cap 506 in the proximal direction. Pulling distal end cap 506 in the proximal direction causes distal end 1840 of pusher 1800 to compress implant 100, which tends to cause each of second expandable section 114 and first expandable section 112 to expand into expanded configuration 402.

Lips 2310 are sized such that implant lumen 110 is at most only partially obstructed. For example, lips 2310 are sized to allow passage of inner tube 1610 therethrough.

Figure 25:
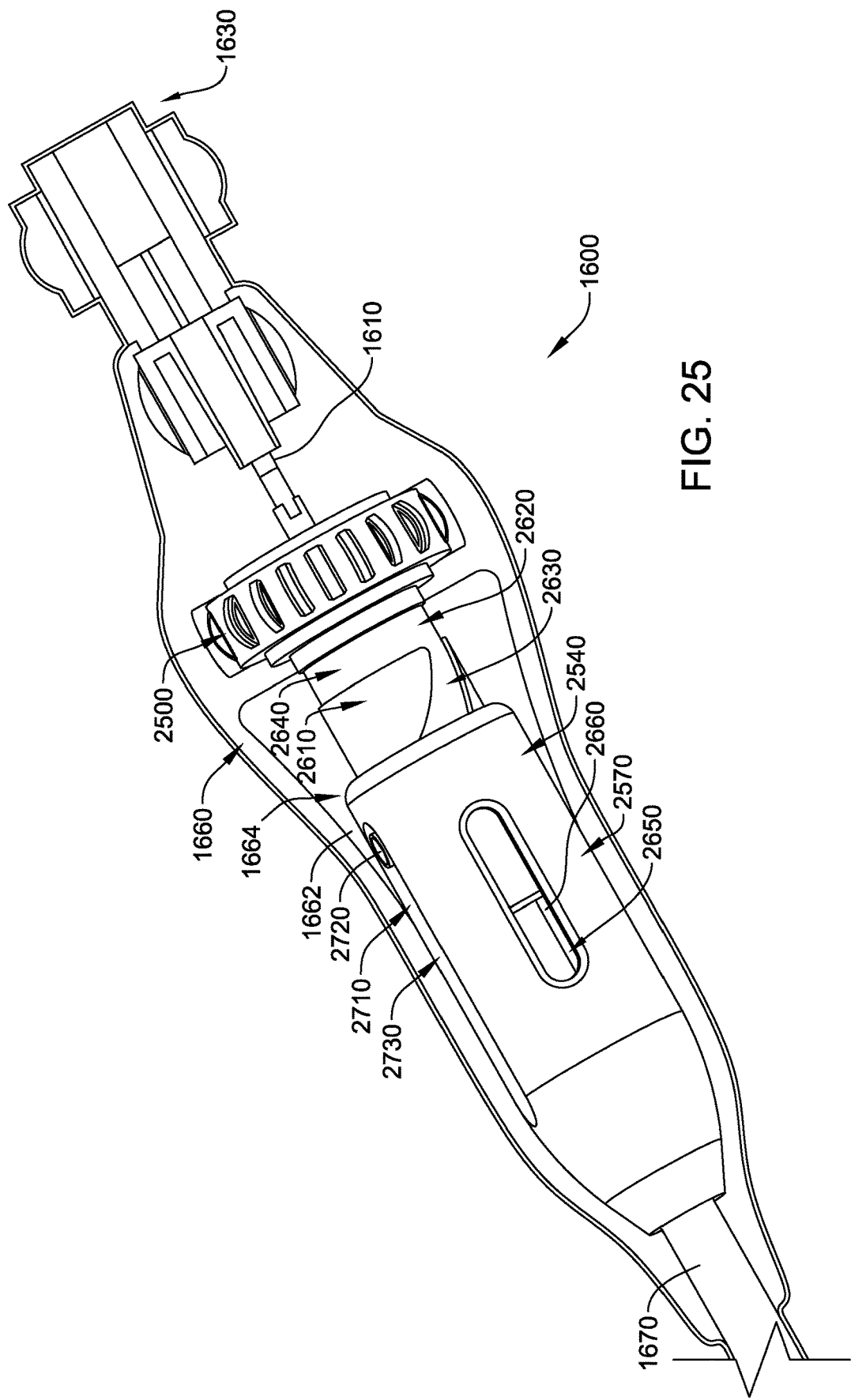
FIG. 25 is a first cut-away view of an alternative embodiment of a delivery device that includes a combined actuator.
Figure 26:
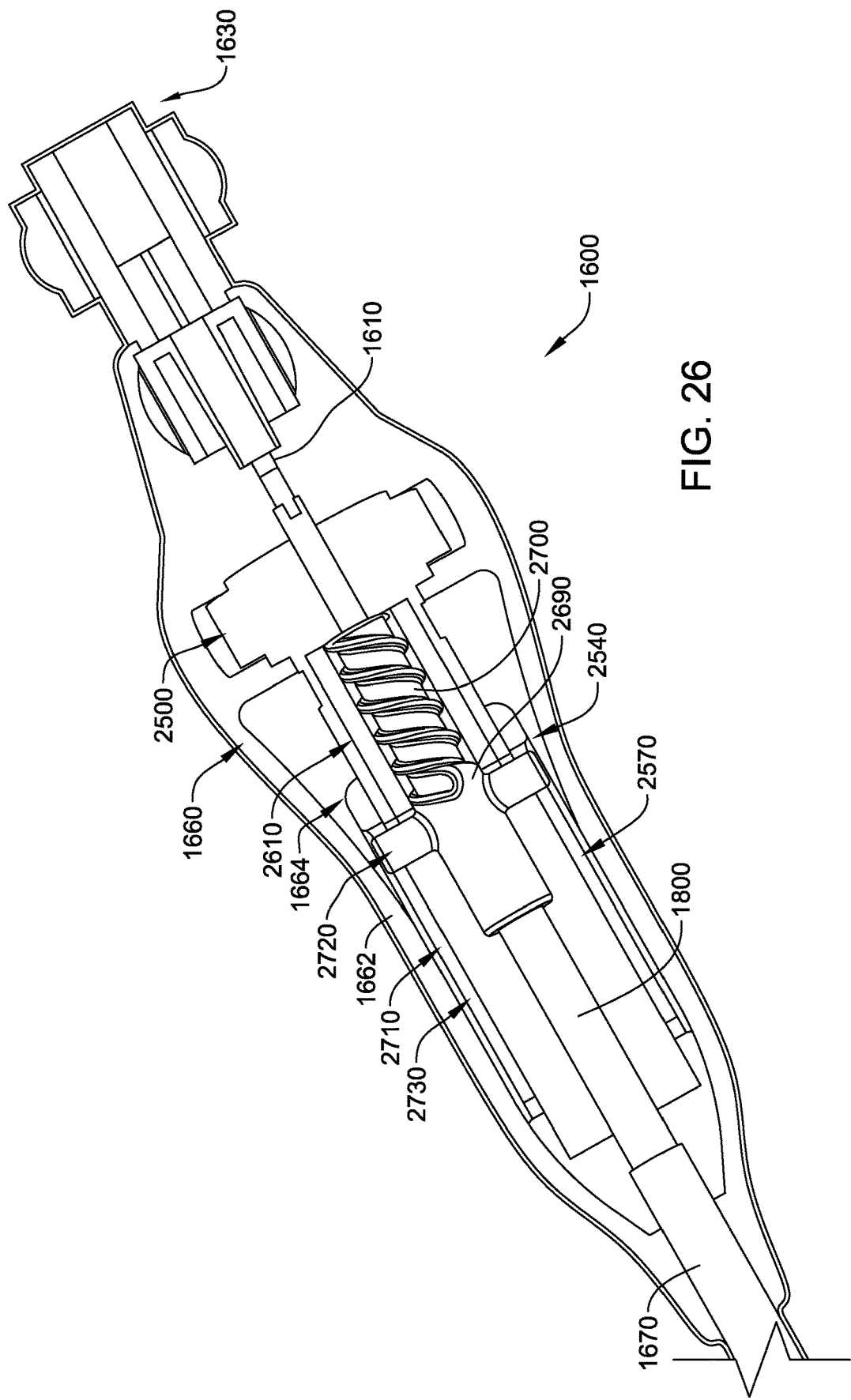
FIG. 26 is a second cut-away view of the delivery device of FIG. 25.

FIGS. 25, 26, and 27 are cut-away views of an alternative embodiment of delivery device 1600 including a combined actuator 2500 operable to move both pusher 1800 and outer tube 1670 longitudinally. With reference to FIGS. 25-27, actuator 2500 is accessible on housing 1660. For example, in the exemplary embodiment, actuator 2500 is a rotatable disk-shaped actuator that is accessible through an aperture in housing 1660, such that a user may grip housing 1660 and use a thumb to rotate actuator 2500 with respect to housing 1660. In the exemplary embodiment, actuator 2500 is operably coupled to each of outer tube 1670 and pusher 1800 via an actuating mechanism 2540 positioned within housing 1660. More specifically, housing 1660 includes a sidewall 1662 that defines a cavity 1664, and actuating mechanism 2540 is positioned within cavity 1664.

Actuating mechanism 2540 includes an outer tube carrier 2570 that is moveable within cavity 1664 between a distal end of cavity 1664 and a proximal end of cavity 1664. More specifically, actuator 2500 is configured to move outer tube carrier 2570 towards the proximal end of cavity 1664 as actuator 2500 is rotated in a first direction (e.g., a clockwise direction when looking from proximal end 1630 towards the distal end of cavity 1664), and to move outer tube carrier 2570 towards the distal end of cavity 1664 as actuator 2500 is rotated in a second direction (e.g., a counterclockwise direction when looking from proximal end 1630 towards the distal end of cavity 1664). In the exemplary embodiment, outer tube carrier 2570 is coupled to outer tube 1670 such that, as outer tube carrier 2570 is moved between the distal end of cavity 1664 and the proximal end of cavity 1664 via operation of actuator 2500, outer tube 1670 moves in the proximal direction, relative to inner tube 1610, from an extended position, shown in FIG. 18, to a retracted position in which implant 100 is exposed.

Actuating mechanism 2540 is configured to convert rotational movement of actuator 2500 into axial movement of outer tube carrier 2570. In the exemplary embodiment, actuating mechanism 2540 further includes a generally tube-shaped body 2610 that extends distally from actuator 2500 and is positioned coaxially with, and received at least partially within, outer tube carrier 2570. A peg (not shown) extending from an inner surface of outer tube carrier 2570 is retained in a groove 2620 defined in an outer surface of body 2610. In the exemplary embodiment, groove 2620 includes a first segment 2630 that extends helically about a central axis of body 2610 and a second segment 2640 that at least partially circumscribes body 2610 at a constant longitudinal position. In the exemplary embodiment, when the peg is received within first segment 2630, outer tube carrier 2570 longitudinally moves with respect to body 2610 between the distal end of cavity 1664 and the proximal end of cavity 1664 as actuator 2500 is rotated. Moreover, in the exemplary embodiment, when the peg is within second segment 2640, outer tube carrier 2570 is substantially longitudinally stationary with respect to body 2610 as actuator 2500 is rotated. In at least some embodiments, second segment 2640 fully circumscribes body 2610 to enable actuator 2500 to be continuously rotated when the peg is within second segment 2640. In some such embodiments, outer tube carrier 2570 is at the proximal end of cavity 1664 when the peg is within second segment 2640.

In the exemplary embodiment, actuating mechanism 2540 further includes a first retaining mechanism 2650 that facilitates preventing outer tube carrier 2570 from rotating with respect to housing 1660 as actuator 2500 is rotated in the first direction and/or in the second direction. In the exemplary embodiment, retaining mechanism 2650 includes a peg (not shown) extending from an inner surface of housing 1660, and a slot 2660 defined in an outer surface of outer tube carrier 2570 and sized to retain the peg. In the exemplary embodiment, slot 2660 extends substantially longitudinally along the outer surface of outer tube carrier 2570, such that outer tube carrier 2570 is longitudinally moveable, while constrained from rotating, with respect to housing 1660 as slot 1660 slides along the peg between a proximal end of slot 1660 and a distal end of slot 1660. Alternatively, outer tube carrier 2570 may be constrained from rotational movement using any mechanism that enables actuating mechanism 2540 to function as described herein.

Alternatively, outer tube 1670 may be moved from the extended position to the retracted position via operation of actuator 2500 using any suitable actuating mechanism that enables outer tube 1670 to function as described herein.

Actuating mechanism 2540 further includes a pusher carrier 2690 that is moveable within cavity 1664 between the proximal and distal ends of cavity 1664. More specifically, actuator 2500 is configured to move pusher carrier 2690 towards the distal end of cavity 1664 as actuator 2500 is rotated in the first direction, and to move pusher carrier 2690 towards the proximal end of cavity 1664 as actuator 2500 is rotated in the second direction. In the exemplary embodiment, pusher carrier 2690 is coupled to pusher 1800 such that, as pusher carrier 2690 is moved between the proximal end of cavity 1664 and the distal end of cavity 1664 via operation of actuator 2500, pusher 1800 moves in the distal direction, relative to inner tube 1610, from a retracted position, shown in FIG. 18, to an extended position in which implant 100 is compressed.

Actuating mechanism 2540 is configured to convert rotational movement of actuator 2500 into axial movement of pusher carrier 2690. In the exemplary embodiment, pusher carrier 2690 is received within a cavity defined by outer tube carrier 2570 and/or body 2610, such that pusher carrier 2690 is disposed coaxially with, and interiorly to, outer tube carrier 2570 and/or body 2610. A peg (not shown) extending from an inner surface of body 2610 is retained in a groove 2700 defined in an outer surface of pusher carrier 2690. In the exemplary embodiment, groove 2700 extends helically about a central axis of pusher carrier 2690 in a direction that is opposite the direction associated with groove 2620. In the exemplary embodiment, pusher 1800 is longitudinally moveable, with respect to inner tube 1610, in a direction that is opposite the direction outer tube carrier 2570 moves with respect to inner tube 1610 as actuator 2500 is rotated. For example, in the exemplary embodiment, actuator 2500 is selectively rotatable in the first direction to simultaneously move outer tube 1670 towards the retracted position and pusher 1800 towards the extended position, or in the second direction to move outer tube 1670 towards the extended position and pusher 1800 towards the retracted position. Groove 2620 extends at a first angle with respect to the longitudinal axis, and groove 2700 extends at a second angle that is different from the first angle. The first angle and/or the second angle are predefined, such that outer tube 1670 is configured to move a first distance with each rotation of actuator 2500, and pusher 1800 is configured to move a second distance with each rotation of actuator 2500 that is less than the first distance.

In the exemplary embodiment, actuating mechanism 2540 further includes a second retaining mechanism 2710 that facilitates preventing pusher carrier 2690 from rotating with respect to outer tube carrier 2570 as actuator 2500 is rotated. In the exemplary embodiment, retaining mechanism 2710 includes a peg 2720 extending from an outer surface of pusher carrier 2690, and a slot 2730 defined in an inner surface of outer tube carrier 2570 sized to retain peg 2720. In the exemplary embodiment, slot 2730 extends substantially longitudinally along the inner surface of outer tube carrier 2570, such that pusher carrier 2690 is longitudinally moveable, while constrained from rotating, with respect to housing 1660 as peg 2720 is moved between a proximal end of slot 2730 and a distal end of slot 2730. Alternatively, pusher carrier 2690 may be moved and/or restricted from movement using any mechanism that enables actuating mechanism 2540 to function as described herein.

Alternatively, pusher 1800 may be moved from the retracted position to the extended position via operation of actuator 2500 using any suitable actuating mechanism that enables pusher 1800 to function as described herein.

In certain embodiments, delivery device 1600 includes actuator 2500 in combination with hypo tube actuator 1710 (shown in FIG. 16). In alternative embodiments, delivery device 1600 includes actuator 2500 in combination with any suitable hypo tube actuation mechanism that enables delivery device 1600 to function as described herein.

Figure 28A:
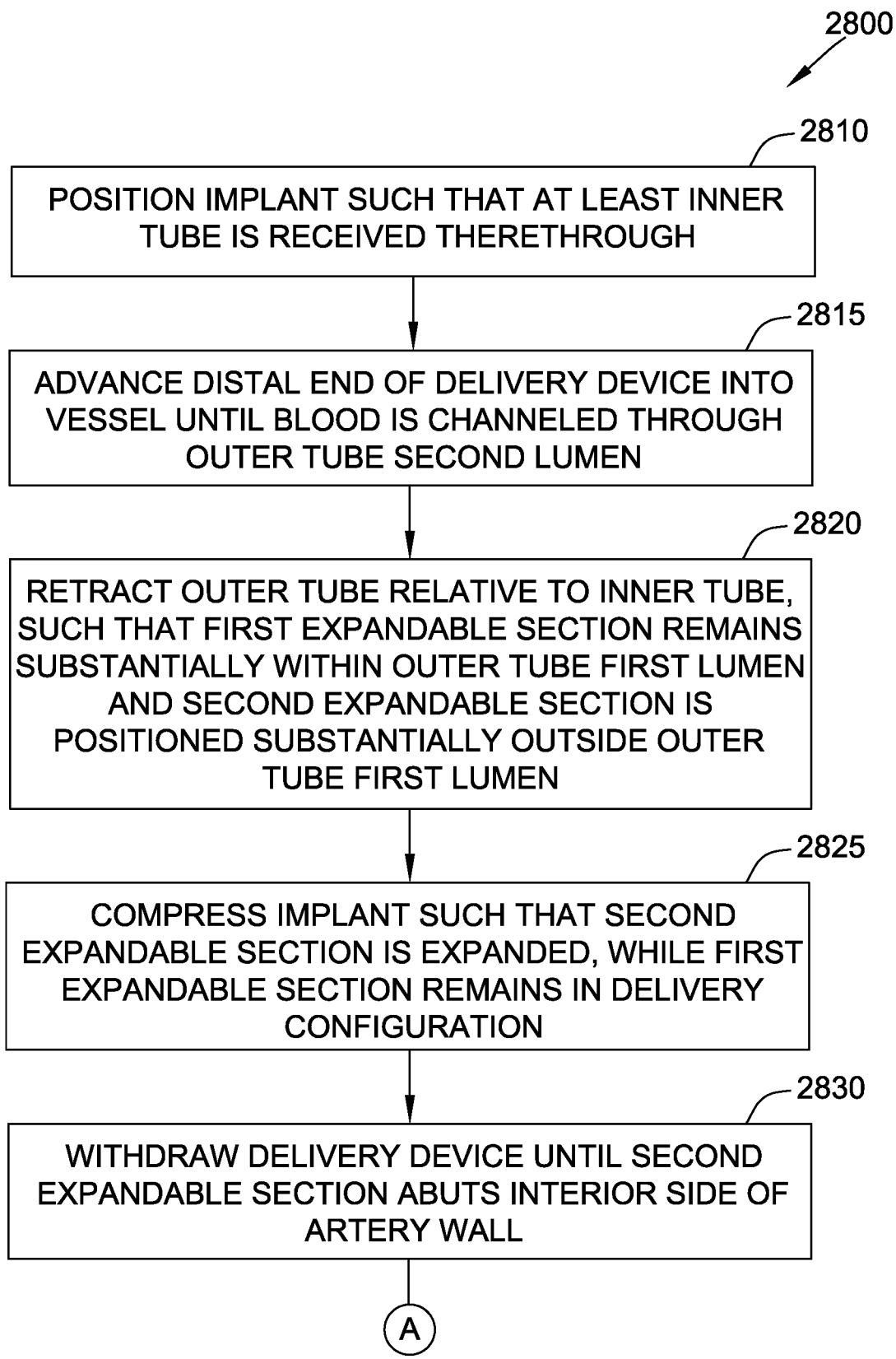
FIG. 28A is a flow diagram of an exemplary method of sealing a puncture of a vessel using an implant, such as the implant shown in any of FIGS. 1-11 and 13-15, deployed by a delivery device, such as the delivery device of FIG. 16.
Figure 28B:
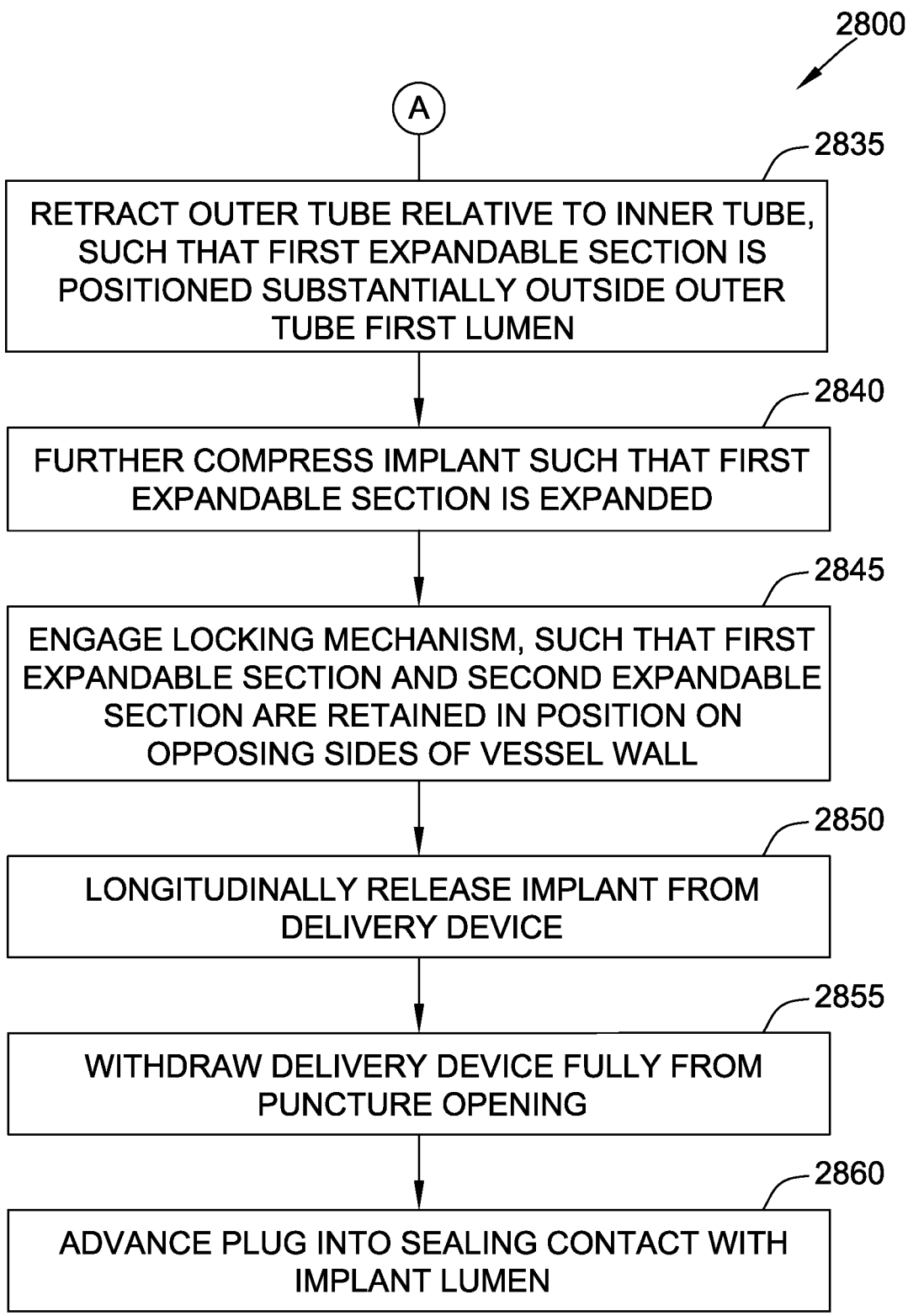
FIG. 28B is a continuation of the flow diagram shown in FIG. 28A.

FIGS. 28A and 28B (collectively referred to as "FIG. 28") are flow diagrams of an exemplary method 2800 of sealing a puncture of a vessel using an implant, such as implant 100 shown in any of FIGS. 1-11 and 13-15, deployed by a delivery device that includes an inner tube and an outer tube circumscribing at least a portion of the inner tube, such as delivery device 1600. FIGS. 29-32 illustrate various stages of method 2800.

Implant 100 is longitudinally retained in delivery configuration 102 within outer tube first lumen 1672 (shown in FIG. 3). For example, outer tube 1670 is positioned in the extended position with respect to inner tube 1610, such that each of first and second expandable sections 112 and 114 of implant 100 are positioned within outer tube first lumen 1672. Additionally, for example, expandable section 1720 of hypo tube 1700 is positioned in the stopper configuration (shown in FIG. 18) to facilitate retaining implant 100 within outer tube first lumen 1672. Alternatively, device 1600 includes inner tube 2100 in lieu of hypo tube 1700, and integral expandable portion 2120 is positioned in the stopper configuration (shown in FIG. 22) to facilitate retaining distal end 106 of implant 100. Alternatively, delivery device 1600 includes hypo tube 2300 in lieu of hypo tube 1700 and implant 100 includes distal end cap 506, and hypo tube 2300 is in the first orientation, such that lips 2310 are coupled to distal end cap 506 (as shown in FIG. 24), to facilitate retaining distal end 106 of implant 100. In the exemplary implementation, implant 100 is positioned 2810 such that at least inner tube 1610, or alternatively at least inner tube 2100, is received therethrough.

During operation, inner tube 1610 is aligned such that a guidewire 2902 extends through inner tube proximal opening 1618 and distal opening 1616. Distal end 1640 is advanced 2815 through subcutaneous tissue 2904 into lumen 2908 of vessel 2900, such as by advancing delivery device 1600 along guidewire 2902, until blood is channeled through outer tube distal opening 1684 and outer tube second lumen 1682 (shown in FIG. 16) and discharged from outer tube proximal opening 1686. In the exemplary embodiment, the blood discharge (i.e., reflux) from proximal opening 1686 is a visual indication that outer tube distal opening 1684, and thus implant 100 retained within outer tube first lumen 1672 longitudinally one of (i) adjacent distal opening 1684 and (ii) distal to distal opening 1684, are positioned within the vessel, as shown in FIG. 29. Proximal portion 1676 of outer tube 1670 facilitates at least partially sealing puncture opening 2906 at this step, and bears against an inferior flap 2912 created by puncture opening 2906 in vessel wall 2910.

In the exemplary embodiment, outer tube 1670 is retracted 2820 relative to inner tube 1610, such that second expandable section 114 is positioned substantially outside of outer tube first lumen 1672, while first expandable section 112 remains positioned substantially within outer tube first lumen 1672. For example, in some embodiments, outer tube actuator 1690 (shown in FIG. 16) is operated to retract 2820 outer tube 1670. For another example, in some embodiments, combined actuator 2500 (shown in FIG. 25) is operated to both retract 2820 outer tube 1670 and advance pusher 1800.

Figure 30:
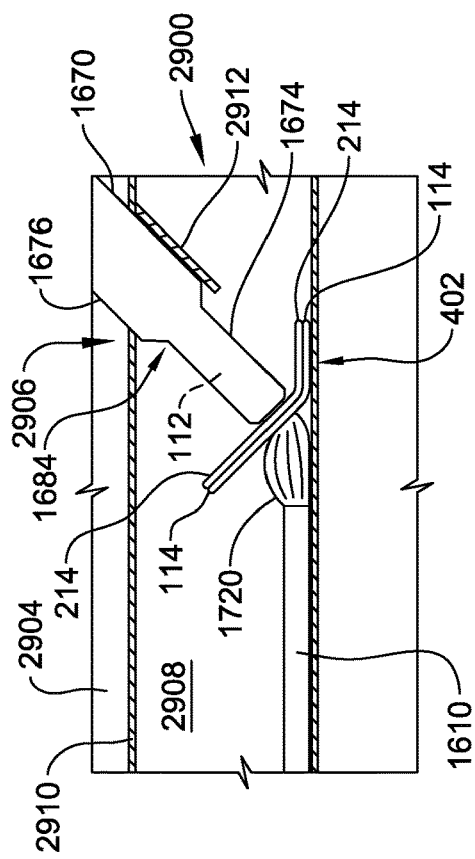
FIG. 30 illustrates a second stage of the method of FIGS. 28A and 28B.

With implant 100 properly positioned, as confirmed by the reflux from proximal opening 1686, distal end 1840 of pusher 1800 compresses 2825 implant 100 such that second expandable section 114 is expanded into expanded configuration 402, while first expandable section 112 remains in the delivery configuration, as shown in FIG. 30. More specifically, because first expandable section 112 of implant 100 remains substantially covered by distal portion 1674 of outer tube 1670, and is thus constrained from expanding, the compressive force exerted by distal end 1840 of pusher 1800 on implant 100 selectively expands only second expandable section 114, which is unconstrained from expansion due to its position substantially outside outer tube first lumen 1672.

In certain embodiments, the step of compressing 2825 implant 100 includes advancing pusher 1800 distally. For example, in some such embodiments, pusher actuator 1810 (shown in FIG. 16) is operated to advance pusher 1800 and compress 2825 implant 100. For another example, in some such embodiments, combined actuator 2500 (shown in FIG. 25) is operated to both retract 2820 outer tube 1670 and advance pusher 1800. In other embodiments, delivery device 1600 includes hypo tube 2300, and the step of compressing 2825 implant 100 includes retracting hypo tube 2300, such that implant 100 is pulled against distal end 1840 of stationary pusher 1800.

In the exemplary embodiment, implant 100 includes skirt 200 (shown in any of FIGS. 2-7, 9-11) or skirt (shown in FIGS. 13-15), and skirt second portion 214 or skirt 1400, respectively, is urged outward into expanded configuration 202 (shown in FIG. 2) or 1404 (shown in FIG. 15) by the expansion of second expandable section 114.

Figure 31:
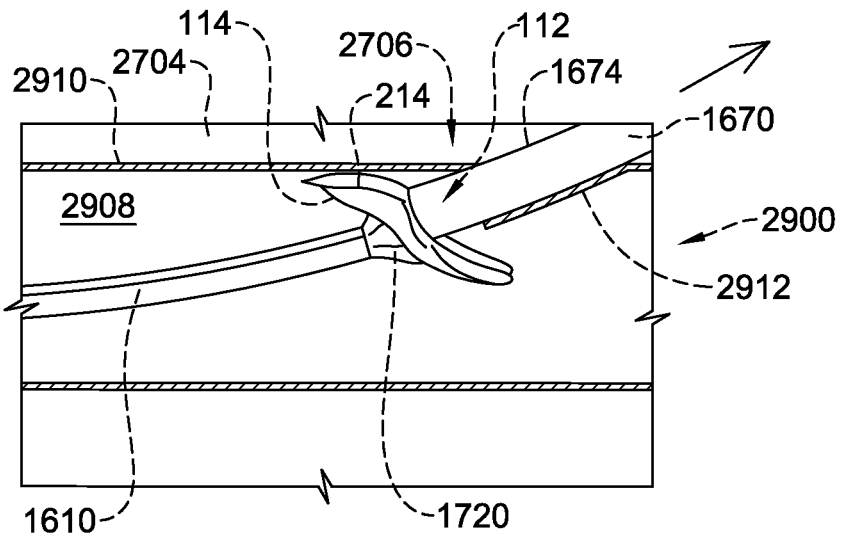
FIG. 31 illustrates a third stage of the method of FIGS. 28A and 28B.

Delivery device 1600 is then withdrawn 2830 in the proximal direction, as shown in FIG. 31, until resistance is encountered as second expandable section 114 abuts the interior side of artery wall 2910. It should be understood that in certain embodiments, the description of second expandable section 114 abutting the interior side of artery wall 2910 includes skirt second portion 214 or, alternatively, skirt 1400 positioned between second expandable section 114 and the interior side of artery wall 2910, such that second expandable section 114 may not be in direct contact with artery wall 2910. In certain embodiments, outer diameter 1680 of outer tube distal portion 1674 is sized to enable inferior flap 2912 to move back toward artery wall 2910, which in turn enables expanded second expandable section 114 to engage inferior flap 2912 as second expandable section 114 is pulled up against the inside of artery wall 2910.

With second expandable section 114 positioned adjacent the interior side of artery wall 2910, first expandable section 112 of implant 100 is located just outside artery wall 2910. Outer tube 1670 is further retracted 2835 relative to inner tube 1610 such that first expandable section 112 is positioned substantially outside outer tube first lumen 1672. For example, delivery device includes outer tube actuator 1690 and pusher actuator 1810, or alternatively combined actuator 2500, operable to further retract 2835 outer tube 1670 as described above.

In addition, distal end 1840 of pusher 1800 further compresses 2840 implant 100, such that first expandable section 112 is expanded into expanded configuration 402. In certain embodiments, the step of further compressing 2840 implant 100 again includes advancing pusher 1800 distally, such as by operating pusher actuator 1810 (shown in FIG. 16) or combined actuator 2500 (shown in FIG. 25) as described above. In other embodiments, the step of further compressing 2840 implant 100 again includes retracting hypo tube 2300, pulling implant 100 against distal end 1840 of stationary pusher 1800, as described above.

Figure 32:
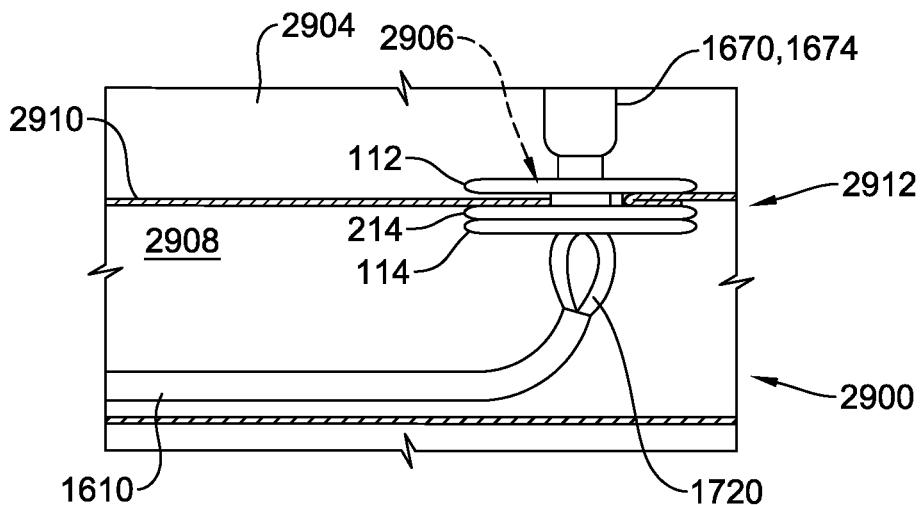
FIG. 32 illustrates a fourth stage of the method of FIGS. 28A and 28B.

In some embodiments, implant 100 includes a suitable locking mechanism, such as but not limited to one of locking mechanism 500 (shown in FIGS. 5-8), locking mechanism 900 (shown in FIGS. 9-11), and locking mechanism 1500 (shown in FIGS. 13-15), and further compressing 2840 implant 100 also includes engaging 2845 the locking mechanism, such that first expandable section 112 and second expandable section 114 are retained in position on opposing sides of vessel wall 2910, as shown in FIG. 32. First expandable section 112, second expandable section 114, and/or skirt 200 of implant 100 cooperate to substantially occlude puncture opening 2906 in vessel wall 2910.

After implant 100 is suitably positioned across vessel wall 2910, implant 100 is then longitudinally released 2850 from delivery device 1600. For example, in some embodiments, expandable section 1720 of hypo tube 1700 is actuated to the neutral configuration, such as by operating actuator 1710, to release 2850 implant 100. For another example, in some embodiments, integral expandable section 2120 of alternative inner tube 2100 is actuated to the neutral configuration, such as by operating an actuator as described above, to release 2850 implant 100. For another example, in some embodiments, alternative hypo tube 2300 is rotated from the first orientation to the second orientation, such that lips 2310 disengage legs 508 of distal end cap 506, to release 2850 implant 100.

After implant 100 is longitudinally released 2850, delivery device 1600 is then fully withdrawn 2855 from puncture opening 2906 and subcutaneous tissue 2904. In some embodiments, plug 800 or a similar plug is advanced 2860 into sealing contact with implant lumen 110, as described above.

In certain embodiments, prior to or during withdrawal 2855 of delivery device 1600, outer tube 1670 is detached from housing 1660 using detachment mechanism 1698 (shown in FIG. 29), such that the portion of outer tube 1670 distal of the distal end of housing 1660 is uncoupled from housing 1660. More specifically, outer tube 1670 is detached to facilitate extraction from puncture opening 2906, through outer tube first lumen 1672 (shown in FIG. 3), of inner tube 1610, hypo tube 1700, and pusher 1800, or alternatively of inner tube 1610, hypo tube 2300, and pusher 1800, or alternatively of inner tube 2100 and pusher 1800. For example, a user maintains forward pressure on detached outer tube 1670 while withdrawing the other components of delivery device 1600 through outer tube first lumen 1672. The user then withdraws the remaining distal portion of outer tube 1670 from puncture opening 2906 and subcutaneous tissue 2904. Alternatively, delivery device 1600 is fully withdrawn 2855 from puncture opening 2906 and subcutaneous tissue 2904 in any suitable fashion. The user then applies pressure over puncture opening 2906 until homeostasis is achieved.

The methods and systems described herein provide advantages as compared to at least some prior methods and systems for sealing a puncture of a vessel, and in particular, but not by way of limitation, for sealing a large-bore opening in a vessel, such as one caused by a catheter introducer of 9 Fr to 24 Fr diameter. Specifically, the system includes an implant deployed by a delivery device. The exemplary implant includes first and second expandable sections that form occluding wings on opposing sides of the puncture site. The exemplary delivery device includes an inner tube and a circumscribing outer tube, with the implant initially retained in a delivery configuration within a first lumen of the outer tube. As the delivery device is advanced into the vessel through the puncture site, reflux through a second lumen of the outer tube immediately indicates when the device is positioned sufficiently within the vessel to permit expansion of one section of the implant, thus reducing a distance that the expanded implant must be drawn back within the vessel towards the puncture site and, consequently, reducing a risk that the expanded implant will encounter a premature obstacle inside the vessel such as plaque, a smaller side branch of the artery, or the walls of the artery itself. In addition, a distal portion of the outer tube has a reduced diameter, such that when the initially expanded section is drawn back against the interior wall of the vessel, an inferior flap created by the insertion of the catheter introducer is permitted to move back towards the puncture opening, thereby reducing a risk that the inferior flap will obstruct the implant as it is pulled towards the inner wall of the artery, preventing a sufficient seal of the puncture site.

Moreover, the mechanical operation enables the two expandable portions of the implant to be selectively expanded at different times and locations during the procedure using the same compressive mechanism. Specifically, the outer tube is selectively retractable with respect to the inner tube to first expose only one of the expandable sections of the implant, such that only the one section can be expanded by the compressive force applied by the delivery device, and second to expose the other expandable section, such that the other section can then be expanded by the compressive force applied by the same mechanism. In some embodiments, each retraction of the outer tube and corresponding application of the compressive force are applied by a single combined actuator, further simplifying operation of the device.

Exemplary embodiments of medical devices are described above in detail. The methods and systems are not limited to the specific embodiments described herein, but rather, operations of the methods and components of the systems may be utilized independently and separately from other operations and/or components described herein. For example, the methods and apparatus described herein may have other industrial and/or consumer applications and are not limited to practice with medical devices as described herein. Rather, one or more embodiments may be implemented and utilized in connection with other industries.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system to facilitate sealing a puncture of a vessel, said system comprising:
   an implant comprising an implant distal end, a first expandable section, and a second expandable section; and
   a delivery device comprising:
   an inner tube comprising (i) an inner tube distal end and (ii) an expandable portion adjacent said inner tube distal end, wherein said expandable portion is selectively actuatable between (i) a stopper configuration that defines a retaining lip, such that said implant distal end is retained on said inner tube proximally of said retaining lip, and (ii) a neutral configuration configured to release said implant distally over said inner tube;
   an outer tube circumscribing at least a portion of said inner tube, said outer tube defining a first lumen configured to retain said implant in a delivery configuration and a second lumen configured to channel a fluid from the vessel through a distal opening of said second lumen, said distal opening longitudinally located one of (i) adjacent to said implant and (ii) proximal to said implant; and
   a pusher circumscribed at least partially by said outer tube, said pusher configured to compress said implant to selectively expand each of said second expandable section and said first expandable section, wherein said outer tube is selectively retractable relative to said inner tube such that said first expandable section remains substantially within said first lumen and said second expandable section is positioned outside of said first lumen, and wherein said outer tube is further selectively retractable relative to said inner tube such that said first expandable section is positioned outside of said first lumen.

2. The system in accordance with claim 1, wherein said implant further comprises a locking mechanism configured to retain said first expandable section and said second expandable section in position on opposing sides of the vessel wall.

3. The system in accordance with claim 2, wherein said locking mechanism comprises a first plurality of resilient flanges extending from a middle ring of said implant towards a proximal ring of said implant, and a second plurality of resilient flanges extending from said middle ring towards a distal ring of said implant, each of said first plurality of resilient flanges including a tooth configured to slide past and engage a lip of said proximal ring, each of said second plurality of resilient flanges including a tooth configured to slide past and engage a lip of said distal ring.

4. The system in accordance with claim 1, wherein said delivery device further comprises a pusher actuator coupled to said pusher and accessible on a housing of said delivery device, said pusher actuator operable to advance said pusher distally to compress said implant.

5. The system in accordance with claim 1, wherein said delivery device further comprises a combined actuator accessible on a housing of said delivery device and coupled to each of said pusher and said outer tube, said combined actuator operable to at least partially simultaneously (i) advance said pusher distally, and (ii) retract said outer tube relative to said inner tube.

6. The system in accordance with claim 1, wherein said implant further comprises an implant proximal end and said pusher further comprises a pusher distal end, and wherein said pusher is movable distally such that said pusher distal end bears against said implant proximal end while said implant distal end is retained against said retaining lip.

7. The system in accordance with claim 1, wherein said expandable portion is integral to said inner tube.

8. The system in accordance with claim 7, wherein said inner tube further comprises longitudinal cuts spaced circumferentially thereabout and extending radially therethrough, said longitudinal cuts define a plurality of expandable struts, and said expandable struts define said expandable portion.

9. The system in accordance with claim 8, wherein said inner tube further comprises a plurality of circumferential cuts extending radially therethrough, alternating pairs of said longitudinal cuts are joined at proximal ends thereof by a respective one of said circumferential cuts, and each of said alternating pairs defines a respective one of said plurality of expandable struts therebetween.

10. The system in accordance with claim 9, wherein a distal end of each of said expandable struts is fixed relative to said inner tube distal end.

11. The system in accordance with claim 10, further comprising:
    a plurality of connectors, each of said connectors disposed on a corresponding one of said expandable struts; and
    an actuator accessible on a housing of said delivery device, wherein said plurality of connectors is configured to cooperate with said actuator to move proximal ends of said expandable struts longitudinally relative to said inner tube distal end.

12. The system in accordance with claim 11, wherein said plurality of connectors comprises pegs extending radially outward from said inner tube, and said actuator comprises slots defined therein and configured to receive said pegs therein.

13. The system in accordance with claim 11, wherein said expandable struts are configured to bulge radially outward to define the stopper configuration in response to movement of said connectors distally by said actuator.

14. The system in accordance with claim 13, wherein said expandable struts are configured to return from the stopper configuration to the neutral configuration in response to movement of said connectors proximally by said actuator.

* * * * *